United States Patent
Jain et al.

(10) Patent No.: US 11,325,945 B2
(45) Date of Patent: May 10, 2022

(54) PEPTIDE BASED PCSK9 VACCINE

(71) Applicant: CADILA HEALTHCARE LIMITED, Gujarat (IN)

(72) Inventors: Mukul Jain, Gujarat (IN); Suresh Giri, Gujarat (IN); Rajesh Bahekar, Gujarat (IN); Gaurav Gupta, Gujarat (IN); Rajendra Chopade, Gujarat (IN)

(73) Assignee: CADILA HEALTHCARE LIMITED, Gujarat (IN)

(*) Notice: Subject to any disclaimer, the term of this patent is extended or adjusted under 35 U.S.C. 154(b) by 202 days.

(21) Appl. No.: 16/498,084

(22) PCT Filed: Apr. 12, 2018

(86) PCT No.: PCT/IB2018/052555
§ 371 (c)(1),
(2) Date: Sep. 26, 2019

(87) PCT Pub. No.: WO2018/189705
PCT Pub. Date: Oct. 18, 2018

(65) Prior Publication Data
US 2020/0399311 A1    Dec. 24, 2020

(30) Foreign Application Priority Data
Apr. 12, 2017  (IN) .............. 201721013281

(51) Int. Cl.
| | | |
|---|---|---|
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| A61K 38/00 | (2006.01) |
| A61P 9/10 | (2006.01) |
| C07K 14/47 | (2006.01) |
| A61P 3/06 | (2006.01) |
| A61P 9/00 | (2006.01) |
| A61K 38/10 | (2006.01) |
| C07K 7/08 | (2006.01) |
| A61K 39/385 | (2006.01) |
| C12N 9/64 | (2006.01) |
| A61K 39/00 | (2006.01) |

(52) U.S. Cl.
CPC .............. *C07K 7/08* (2013.01); *A61K 38/005* (2013.01); *A61K 38/10* (2013.01); *A61K 39/385* (2013.01); *C12N 9/6454* (2013.01); *A61K 2039/575* (2013.01); *A61K 2039/6037* (2013.01)

(58) Field of Classification Search
None
See application file for complete search history.

(56) References Cited

U.S. PATENT DOCUMENTS 8,889,144 B2 * 11/2014 Champion ........... C12N 9/6424
424/197.11

FOREIGN PATENT DOCUMENTS

WO    2011027257 A3    3/2011
WO    2014033158 A2    3/2014

OTHER PUBLICATIONS

Gentilucci, et al., Curr. Pharm. Design 16:3185-3203 (2010) (Year: 2010).*
Akahoshi et al., Biochem. Biophys. Res. Commun. 414:625-630 (2011) (Year: 2011).*
Adessi et al., Curr. Med. Chem. 9:963-978 (2002) (Year: 2002).*
Tombling et al., Atherosclerosis 330:52-60 (2021) (Year: 2021).*
Nediljko Budisa; Prolegomena to future experimental efforts on genetic code engineering by expanding its amino acid repertoire; 38 Pages; 2004 Wiley-VCH Verlag GmbH & Co., KGaA, Weinheim; Dec. 3, 2004.

* cited by examiner

*Primary Examiner* — Thea D'Ambrosio
(74) *Attorney, Agent, or Firm* — Renner, Kenner, Greive, Bobak, Taylor & Weber

(57) ABSTRACT

The present invention relates to novel short chain peptides of formula (I) which can be useful as a vaccine when in conjugation with suitable immunogenic carrier and suitable adjuvant. These are useful for the treatment for the PCSK9 mediated diseases.

$$A\text{-}Z_1\text{-}Z_2\text{-}Z_3\text{-}Z_4\text{-}Z_5\text{-}Z_6\text{-}Z_7\text{-}Z_8\text{-}Z_9\text{-}Z_{10}\text{-}Z_{11}\text{-}Z_{12}\text{-}B \quad \text{Formula (I)}$$

5 Claims, No Drawings

Specification includes a Sequence Listing.

SEQUENCE LISTING

```
<160> NUMBER OF SEQ ID NOS: 58

<210> SEQ ID NO 1
<211> LENGTH: 12
<212> TYPE: PRT
<213> ORGANISM: Artificial
<220> FEATURE:
<223> OTHER INFORMATION: PCSK9

<400> SEQUENCE: 1

Ser Ile Pro Trp Asn Leu Glu Arg Ile Thr Pro Cys
1               5                   10

<210> SEQ ID NO 2
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: PEPTIDE
<222> LOCATION: (2)..(2)
<223> OTHER INFORMATION: Xaa is Norleucine

<400> SEQUENCE: 2

Ser Xaa Pro Trp Asn Leu Glu Arg Ile Thr Pro Cys
1               5                   10

<210> SEQ ID NO 3
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: PEPTIDE
<222> LOCATION: (2)..(2)
<223> OTHER INFORMATION: Xaa is alpha-Amino-isobutyric acid

<400> SEQUENCE: 3

Ser Xaa Pro Trp Asn Leu Glu Arg Ile Thr Pro Cys
1               5                   10

<210> SEQ ID NO 4
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: PEPTIDE
<222> LOCATION: (9)..(9)
<223> OTHER INFORMATION: Xaa is Norleucine

<400> SEQUENCE: 4

Ser Ile Pro Trp Asn Leu Glu Arg Xaa Thr Pro Cys
1               5                   10

<210> SEQ ID NO 5
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (9)..(9)
<223> OTHER INFORMATION: Xaa is alpha-Amino-isobutyric acid

<400> SEQUENCE: 5
```

```
Ser Ile Pro Trp Asn Leu Glu Arg Xaa Thr Pro Cys
1               5                   10
```

<210> SEQ ID NO 6
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (8)..(8)
<223> OTHER INFORMATION: Xaa is homoarginine

<400> SEQUENCE: 6

```
Ser Ile Pro Trp Asn Leu Glu Xaa Ile Thr Pro Cys
1               5                   10
```

<210> SEQ ID NO 7
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (6)..(6)
<223> OTHER INFORMATION: Xaa is Norleucine

<400> SEQUENCE: 7

```
Ser Ile Pro Trp Asn Xaa Glu Arg Ile Thr Pro Cys
1               5                   10
```

<210> SEQ ID NO 8
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline

<400> SEQUENCE: 8

```
Ser Ile Xaa Trp Asn Leu Glu Arg Ile Thr Pro Cys
1               5                   10
```

<210> SEQ ID NO 9
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (11)..(11)
<223> OTHER INFORMATION: Xaa is 4-Hydroxyproline

<400> SEQUENCE: 9

```
Ser Ile Pro Trp Asn Leu Glu Arg Ile Thr Xaa Cys
1               5                   10
```

<210> SEQ ID NO 10
<211> LENGTH: 12
<212> TYPE: PRT
<213> ORGANISM: Artificial
<220> FEATURE:
<223> OTHER INFORMATION: PCSK9

```
<220> FEATURE:
<221> NAME/KEY: Xaa
<222> LOCATION: (6)..(6)
<223> OTHER INFORMATION: Xaa is alpha-Amino-isobutyric acid

<400> SEQUENCE: 10

Ser Ile Pro Trp Asn Xaa Glu Arg Ile Thr Pro Cys
1               5                   10

<210> SEQ ID NO 11
<211> LENGTH: 13
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (1)..(1)
<223> OTHER INFORMATION: Xaa is Acetyl

<400> SEQUENCE: 11

Xaa Ser Ile Pro Trp Asn Leu Glu Arg Ile Thr Pro Cys
1               5                   10

<210> SEQ ID NO 12
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (8)..(8)
<223> OTHER INFORMATION: Xaa is Citrulline

<400> SEQUENCE: 12

Ser Ile Pro Trp Asn Leu Glu Xaa Ile Thr Pro Cys
1               5                   10

<210> SEQ ID NO 13
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (10)..(10)
<223> OTHER INFORMATION: Xaa is alpha-Amino-isobutyric acid

<400> SEQUENCE: 13

Ser Ile Pro Trp Asn Leu Glu Arg Ile Xaa Pro Cys
1               5                   10

<210> SEQ ID NO 14
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (1)..(1)
<223> OTHER INFORMATION: Xaa is alpha-Amino-isobutyric acid

<400> SEQUENCE: 14

Xaa Ile Pro Trp Asn Leu Glu Arg Ile Thr Pro Cys
1               5                   10
```

```
<210> SEQ ID NO 15
<211> LENGTH: 13
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (2)..(2)
<223> OTHER INFORMATION: Xaa is N-methyl-isoleucine

<400> SEQUENCE: 15

Ser Xaa Ile Pro Trp Asn Leu Glu Arg Ile Thr Pro Cys
1               5                   10

<210> SEQ ID NO 16
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (6)..(6)
<223> OTHER INFORMATION: xaa is N-methyl-leucine

<400> SEQUENCE: 16

Ser Ile Pro Trp Asn Xaa Glu Arg Ile Thr Pro Cys
1               5                   10

<210> SEQ ID NO 17
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (9)..(9)
<223> OTHER INFORMATION: Xaa is N-methyl-isoleucine

<400> SEQUENCE: 17

Ser Ile Pro Trp Asn Leu Glu Arg Xaa Thr Pro Cys
1               5                   10

<210> SEQ ID NO 18
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (4)..(4)
<223> OTHER INFORMATION: Xaa is 2-Aminophenyl pentanoic acid

<400> SEQUENCE: 18

Ser Ile Pro Xaa Asn Leu Glu Arg Ile Thr Pro Cys
1               5                   10

<210> SEQ ID NO 19
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (4)..(4)
<223> OTHER INFORMATION: Xaa is
      (S)-2-amino-3-(2'-ethyl-4'-methoxy-[1,1'-biphenyl]-4-yl)propanoic
``` acid

<400> SEQUENCE: 19

Ser Ile Pro Xaa Asn Leu Glu Arg Ile Thr Pro Cys
1               5                   10

<210> SEQ ID NO 20
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (9)..(9)
<223> OTHER INFORMATION: Xaa is alpha-Amino-isobutyric acid

<400> SEQUENCE: 20

Ser Ile Xaa Trp Asn Leu Glu Arg Xaa Thr Pro Cys
1               5                   10

<210> SEQ ID NO 21
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (6)..(6)
<223> OTHER INFORMATION: Xaa is alpha-Amino-isobutyric acid

<400> SEQUENCE: 21

Ser Ile Xaa Trp Asn Xaa Glu Arg Ile Thr Pro Cys
1               5                   10

<210> SEQ ID NO 22
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (8)..(8)
<223> OTHER INFORMATION: Xaa is Citrulline
<220> FEATURE:
<221> NAME/KEY: Xaa
<222> LOCATION: (9)..(9)
<223> OTHER INFORMATION: Xaa is alpha-Amino-isobutyric acid

<400> SEQUENCE: 22

Ser Ile Pro Trp Asn Leu Glu Xaa Xaa Thr Pro Cys
1               5                   10

<210> SEQ ID NO 23
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa

```
<222> LOCATION: (6)..(6)
<223> OTHER INFORMATION: Xaa is alpha-Amino-isobutyric acid
<220> FEATURE:
<221> NAME/KEY: Xaa
<222> LOCATION: (8)..(8)
<223> OTHER INFORMATION: Xaa is Citrulline

<400> SEQUENCE: 23

Ser Ile Pro Trp Asn Xaa Glu Xaa Ile Thr Pro Cys
1               5                   10

<210> SEQ ID NO 24
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (8)..(8)
<223> OTHER INFORMATION: Xaa is Citrulline

<400> SEQUENCE: 24

Ser Ile Xaa Trp Asn Leu Glu Xaa Ile Thr Pro Cys
1               5                   10

<210> SEQ ID NO 25
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (6)..(6)
<223> OTHER INFORMATION: Xaa is alpha-Amino-isobutyric acid
<220> FEATURE:
<221> NAME/KEY: Xaa
<222> LOCATION: (8)..(8)
<223> OTHER INFORMATION: Xaa is Citrulline

<400> SEQUENCE: 25

Ser Ile Xaa Trp Asn Xaa Glu Xaa Ile Thr Pro Cys
1               5                   10

<210> SEQ ID NO 26
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (8)..(8)
<223> OTHER INFORMATION: Xaa is Citrulline
<220> FEATURE:
<221> NAME/KEY: Xaa
<222> LOCATION: (9)..(9)
<223> OTHER INFORMATION: Xaa is alpha-Amino-isobutyric acid

<400> SEQUENCE: 26
```

```
Ser Ile Xaa Trp Asn Leu Glu Xaa Xaa Thr Pro Cys
1               5                   10

<210> SEQ ID NO 27
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (8)..(8)
<223> OTHER INFORMATION: Xaa is Citrulline
<220> FEATURE:
<221> NAME/KEY: Xaa
<222> LOCATION: (11)..(11)
<223> OTHER INFORMATION: Xaa is 4-Hydroxyproline

<400> SEQUENCE: 27

Ser Ile Pro Trp Asn Leu Glu Xaa Ile Thr Xaa Cys
1               5                   10

<210> SEQ ID NO 28
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (6)..(6)
<223> OTHER INFORMATION: Xaa is alpha-Amino-isobutyric acid
<220> FEATURE:
<221> NAME/KEY: Xaa
<222> LOCATION: (11)..(11)
<223> OTHER INFORMATION: Xaa is 4-Hydroxyproline

<400> SEQUENCE: 28

Ser Ile Pro Trp Asn Xaa Glu Arg Ile Thr Xaa Cys
1               5                   10

<210> SEQ ID NO 29
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (6)..(6)
<223> OTHER INFORMATION: Xaa is alpha-Amino-isobutyric acid
<220> FEATURE:
<221> NAME/KEY: Xaa
<222> LOCATION: (11)..(11)
<223> OTHER INFORMATION: Xaa is 4-Hydroxyproline

<400> SEQUENCE: 29

Ser Ile Xaa Trp Asn Xaa Glu Arg Ile Thr Xaa Cys
1               5                   10

<210> SEQ ID NO 30
<211> LENGTH: 12
<212> TYPE: PRT
<213> ORGANISM: Artificial
<220> FEATURE:
<223> OTHER INFORMATION: PCSK9
<220> FEATURE:
```

```
<221> NAME/KEY: Xaa
<222> LOCATION: (6)..(6)
<223> OTHER INFORMATION: Xaa is alpha-Amino-isobutyric acid
<220> FEATURE:
<221> NAME/KEY: Xaa
<222> LOCATION: (8)..(8)
<223> OTHER INFORMATION: Xaa is Citrulline
<220> FEATURE:
<221> NAME/KEY: Xaa
<222> LOCATION: (11)..(11)
<223> OTHER INFORMATION: Xaa is 4-Hydroxyproline

<400> SEQUENCE: 30

Ser Ile Pro Trp Asn Xaa Glu Xaa Ile Thr Xaa Cys
1               5                   10

<210> SEQ ID NO 31
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (8)..(8)
<223> OTHER INFORMATION: Xaa is Citrulline
<220> FEATURE:
<221> NAME/KEY: Xaa
<222> LOCATION: (11)..(11)
<223> OTHER INFORMATION: Xaa is 4-Hydroxyproline

<400> SEQUENCE: 31

Ser Ile Xaa Trp Asn Leu Glu Xaa Ile Thr Xaa Cys
1               5                   10

<210> SEQ ID NO 32
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is alpha-methyl-proline
<220> FEATURE:
<221> NAME/KEY: Xaa
<222> LOCATION: (8)..(8)
<223> OTHER INFORMATION: Xaa is Citrulline

<400> SEQUENCE: 32

Ser Ile Xaa Trp Asn Leu Glu Xaa Ile Thr Pro Cys
1               5                   10

<210> SEQ ID NO 33
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 1-amino-cyclopropanecarboxylic acid
<220> FEATURE:
<221> NAME/KEY: Xaa
<222> LOCATION: (8)..(8)
<223> OTHER INFORMATION: Xaa is Citrulline
```

```
<400> SEQUENCE: 33

Ser Ile Xaa Trp Asn Leu Glu Xaa Ile Thr Pro Cys
1               5                   10

<210> SEQ ID NO 34
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 1-amino-cyclopentanecarboxylic acid
<220> FEATURE:
<221> NAME/KEY: Xaa
<222> LOCATION: (8)..(8)
<223> OTHER INFORMATION: Xaa is Citrulline

<400> SEQUENCE: 34

Ser Ile Xaa Trp Asn Leu Glu Xaa Ile Thr Pro Cys
1               5                   10

<210> SEQ ID NO 35
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 1-amino-cyclohexanecarboxylic acid
<220> FEATURE:
<221> NAME/KEY: Xaa
<222> LOCATION: (8)..(8)
<223> OTHER INFORMATION: Xaa is Citrulline

<400> SEQUENCE: 35

Ser Ile Xaa Trp Asn Leu Glu Xaa Ile Thr Pro Cys
1               5                   10

<210> SEQ ID NO 36
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (6)..(6)
<223> OTHER INFORMATION: Xaa is beta alanine
<220> FEATURE:
<221> NAME/KEY: Xaa
<222> LOCATION: (8)..(8)
<223> OTHER INFORMATION: Xaa is Citrulline

<400> SEQUENCE: 36

Ser Ile Xaa Trp Asn Xaa Glu Xaa Ile Thr Pro Cys
1               5                   10

<210> SEQ ID NO 37
<211> LENGTH: 12
<212> TYPE: PRT
<213> ORGANISM: Artificial
<220> FEATURE:
<223> OTHER INFORMATION: PCSK9
```

<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (7)..(7)
<223> OTHER INFORMATION: Xaa is alpha-methyl-glutamic acid
<220> FEATURE:
<221> NAME/KEY: Xaa
<222> LOCATION: (8)..(8)
<223> OTHER INFORMATION: Xaa is Citrulline

<400> SEQUENCE: 37

Ser Ile Xaa Trp Asn Leu Xaa Xaa Ile Thr Pro Cys
1               5                   10

<210> SEQ ID NO 38
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (7)..(7)
<223> OTHER INFORMATION: Xaa is homoglutamic acid
<220> FEATURE:
<221> NAME/KEY: Xaa
<222> LOCATION: (8)..(8)
<223> OTHER INFORMATION: Xaa is Citrulline

<400> SEQUENCE: 38

Ser Ile Xaa Trp Asn Leu Xaa Xaa Ile Thr Pro Cys
1               5                   10

<210> SEQ ID NO 39
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (7)..(7)
<223> OTHER INFORMATION: Xaa is alpha-methyl-aspartic acid
<220> FEATURE:
<221> NAME/KEY: Xaa
<222> LOCATION: (8)..(8)
<223> OTHER INFORMATION: Xaa is Citrulline

<400> SEQUENCE: 39

Ser Ile Xaa Trp Asn Leu Xaa Xaa Ile Thr Pro Cys
1               5                   10

<210> SEQ ID NO 40
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline

```
<220> FEATURE:
<221> NAME/KEY: Xaa
<222> LOCATION: (6)..(6)
<223> OTHER INFORMATION: Xaa is Homoleucine
<220> FEATURE:
<221> NAME/KEY: Xaa
<222> LOCATION: (8)..(8)
<223> OTHER INFORMATION: Xaa is Citrulline

<400> SEQUENCE: 40

Ser Ile Xaa Trp Asn Xaa Glu Xaa Ile Thr Pro Cys
1               5                   10

<210> SEQ ID NO 41
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (6)..(6)
<223> OTHER INFORMATION: Xaa is alpha-methyl-aspartic acid
<220> FEATURE:
<221> NAME/KEY: Xaa
<222> LOCATION: (8)..(8)
<223> OTHER INFORMATION: Xaa is Citrulline

<400> SEQUENCE: 41

Ser Ile Xaa Trp Asn Xaa Glu Xaa Ile Thr Pro Cys
1               5                   10

<210> SEQ ID NO 42
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Thiaproline
<220> FEATURE:
<221> NAME/KEY: Xaa
<222> LOCATION: (8)..(8)
<223> OTHER INFORMATION: Xaa is Citrulline

<400> SEQUENCE: 42

Ser Ile Xaa Trp Asn Leu Glu Xaa Ile Thr Pro Cys
1               5                   10

<210> SEQ ID NO 43
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 2-Thiaproline
<220> FEATURE:
<221> NAME/KEY: Xaa
<222> LOCATION: (8)..(8)
<223> OTHER INFORMATION: Xaa is Citrulline

<400> SEQUENCE: 43

Ser Ile Xaa Trp Asn Leu Glu Xaa Ile Thr Pro Cys
```

```
1               5                   10

<210> SEQ ID NO 44
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 3-Hydroxyproline
<220> FEATURE:
<221> NAME/KEY: Xaa
<222> LOCATION: (8)..(8)
<223> OTHER INFORMATION: Xaa is Citrulline

<400> SEQUENCE: 44

Ser Ile Xaa Trp Asn Leu Glu Xaa Ile Thr Pro Cys
1               5                   10

<210> SEQ ID NO 45
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Aminoproline
<220> FEATURE:
<221> NAME/KEY: Xaa
<222> LOCATION: (8)..(8)
<223> OTHER INFORMATION: Xaa is Citrulline

<400> SEQUENCE: 45

Ser Ile Xaa Trp Asn Leu Glu Xaa Ile Thr Pro Cys
1               5                   10

<210> SEQ ID NO 46
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 3-Aminoproline
<220> FEATURE:
<221> NAME/KEY: Xaa
<222> LOCATION: (8)..(8)
<223> OTHER INFORMATION: Xaa is Citrulline

<400> SEQUENCE: 46

Ser Ile Xaa Trp Asn Leu Glu Xaa Ile Thr Pro Cys
1               5                   10

<210> SEQ ID NO 47
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is3-fluoroproline
<220> FEATURE:
<221> NAME/KEY: Xaa
<222> LOCATION: (8)..(8)
```

<223> OTHER INFORMATION: Xaa is Citrulline

<400> SEQUENCE: 47

Ser Ile Xaa Trp Asn Leu Glu Xaa Ile Thr Pro Cys
1               5                   10

<210> SEQ ID NO 48
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-fluoroproline
<220> FEATURE:
<221> NAME/KEY: Xaa
<222> LOCATION: (8)..(8)
<223> OTHER INFORMATION: Xaa is Citrulline

<400> SEQUENCE: 48

Ser Ile Xaa Trp Asn Leu Glu Xaa Ile Thr Pro Cys
1               5                   10

<210> SEQ ID NO 49
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (1)..(1)
<223> OTHER INFORMATION: Xaa is O-methyl-serine
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (8)..(8)
<223> OTHER INFORMATION: Xaa is Citrulline

<400> SEQUENCE: 49

Xaa Ile Xaa Trp Asn Leu Glu Xaa Ile Thr Pro Cys
1               5                   10

<210> SEQ ID NO 50
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (1)..(1)
<223> OTHER INFORMATION: Xaa is homoserine
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (8)..(8)
<223> OTHER INFORMATION: Xaa is Citrulline

<400> SEQUENCE: 50

Xaa Ile Xaa Trp Asn Leu Glu Xaa Ile Thr Pro Cys
1               5                   10

```
<210> SEQ ID NO 51
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (1)..(1)
<223> OTHER INFORMATION: Xaa is O-methyl-threonine
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (8)..(8)
<223> OTHER INFORMATION: Xaa is Citrulline

<400> SEQUENCE: 51

Xaa Ile Xaa Trp Asn Leu Glu Xaa Ile Thr Pro Cys
1               5                   10

<210> SEQ ID NO 52
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (1)..(1)
<223> OTHER INFORMATION: Xaa is O-methyl-homoserine
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (8)..(8)
<223> OTHER INFORMATION: Xaa is Citrulline

<400> SEQUENCE: 52

Xaa Ile Xaa Trp Asn Leu Glu Xaa Ile Thr Pro Cys
1               5                   10

<210> SEQ ID NO 53
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (4)..(4)
<223> OTHER INFORMATION: Xaa is 2-fluorophenylalanine
<220> FEATURE:
<221> NAME/KEY: Xaa
<222> LOCATION: (8)..(8)
<223> OTHER INFORMATION: Xaa is Citrulline

<400> SEQUENCE: 53

Ser Ile Xaa Xaa Asn Leu Glu Xaa Ile Thr Pro Cys
1               5                   10

<210> SEQ ID NO 54
<211> LENGTH: 12
<212> TYPE: PRT
<213> ORGANISM: Artificial
```

```
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (4)..(4)
<223> OTHER INFORMATION: Xaa is alpha-methyl-phenylalanine
<220> FEATURE:
<221> NAME/KEY: Xaa
<222> LOCATION: (8)..(8)
<223> OTHER INFORMATION: Xaa is Citrulline

<400> SEQUENCE: 54

Ser Ile Xaa Xaa Asn Leu Glu Xaa Ile Thr Pro Cys
1               5                   10

<210> SEQ ID NO 55
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (4)..(4)
<223> OTHER INFORMATION: Xaa is alpha-methyl-2-fluorophenylalanine
<220> FEATURE:
<221> NAME/KEY: Xaa
<222> LOCATION: (8)..(8)
<223> OTHER INFORMATION: Xaa is Citrulline

<400> SEQUENCE: 55

Ser Ile Xaa Xaa Asn Leu Glu Xaa Ile Thr Pro Cys
1               5                   10

<210> SEQ ID NO 56
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (4)..(4)
<223> OTHER INFORMATION: Xaa is alpha-methyl-2,6-diflurophenylalanine
<220> FEATURE:
<221> NAME/KEY: Xaa
<222> LOCATION: (8)..(8)
<223> OTHER INFORMATION: Xaa is Citrulline

<400> SEQUENCE: 56

Ser Ile Xaa Xaa Asn Leu Glu Xaa Ile Thr Pro Cys
1               5                   10

<210> SEQ ID NO 57
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
```

```
<222> LOCATION: (3)..(3)
<223> OTHER INFORMATION: Xaa is 4-Hydroxyproline
<220> FEATURE:
<221> NAME/KEY: Xaa
<222> LOCATION: (4)..(4)
<223> OTHER INFORMATION: Xaa is alpha-methyl- 2-aminophenyl pentanoic
      acid
<220> FEATURE:
<221> NAME/KEY: Xaa
<222> LOCATION: (8)..(8)
<223> OTHER INFORMATION: Xaa is Citrulline

<400> SEQUENCE: 57

Ser Ile Xaa Xaa Asn Leu Glu Xaa Ile Thr Pro Cys
1               5                   10

<210> SEQ ID NO 58
<211> LENGTH: 12
<212> TYPE: PRT
<213> ORGANISM: Artificial
<220> FEATURE:
<223> OTHER INFORMATION: PCSK9
<220> FEATURE:
<221> NAME/KEY: Xaa
<222> LOCATION: (3)..(3)
<223> OTHER INFORMATION: Xaa is 4-Hydroxyproline
<220> FEATURE:
<221> NAME/KEY: Xaa
<222> LOCATION: (7)..(7)
<223> OTHER INFORMATION: Xaa is 2-amino-4-cyanobutanoic acid
<220> FEATURE:
<221> NAME/KEY: Xaa
<222> LOCATION: (8)..(8)
<223> OTHER INFORMATION: Xaa is Citrulline

<400> SEQUENCE: 58

Ser Ile Xaa Trp Asn Leu Xaa Xaa Ile Thr Pro Cys
1               5                   10
```

PEPTIDE BASED PCSK9 VACCINE

FIELD OF INVENTION

The present invention relates to novel short-chain peptides of Formula (I), their enantiomers, their diastereoisomers, their stereoisomers, their pharmaceutically acceptable salts or prodrugs. In an embodiment the peptides of formula (I) are conjugated with suitable immunogenic carrier and useful in the treatment or prevention of diseases mediating through PCSK9 and capable of inducing the formation of antibodies directed to PCSK9 in vivo.

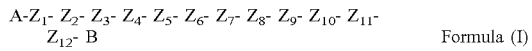

A-$Z_1$- $Z_2$- $Z_3$- $Z_4$- $Z_5$- $Z_6$- $Z_7$- $Z_8$- $Z_9$- $Z_{10}$- $Z_{11}$- $Z_{12}$- B      Formula (I)

The invention also relates to methods for production of these medicaments, immunogenic compositions and pharmaceutical composition thereof and their use in medicine.

BACKGROUND TO THE INVENTION

The present invention relates to novel short-chain peptides. Further, these peptides are conjugated with a suitable immunogenic carrier and are capable of inhibiting the Proprotein Convertase Subtilisin/Kexin Type 9 (PCSK9)-mediated degradation of the Low Density Lipoprotein (LDL) receptor (LDLR). These novel peptides coupled to an immunogenic carrier are formulated as a vaccine for the prevention and/or treatment of PCSK9 associated health disorders like hyperlipidaemia, hypercholesterolemia, or atherosclerosis. These complications lead to the cardiovascular diseases (CVD) which causes morbidity and mortality.

Earlier, the agents such as statins were used as the therapeutic agents for the reduction of plasma Low Density Lipoprotein cholesterol (LDLc). Discovery of PCSK9 and its role in the regulation of plasma LDLc through the enhancement of the degradation of the LDLR led to the realization that PCSK9 is likely to be a feasible target for the control of health disorders like hyperlipidemia, hypercholesterolemia or atherosclerosis.

PCSK9 was discovered in 2003 as the third gene locus associated with Autosomal Dominant Hypercholesterolemia (ADH). PCSK9 is also known as neural apoptosis-regulated convertase 1 (NARC-1), a proteinase k-like subtilase identified as the $9^{th}$ member of the mammalian PCSK family. It is mainly expressed in liver, intestine, and kidney. It is synthesized as a ~72 kDa protein which undergoes autocatalytic cleavage before it is secreted as a ~65 kDa mature protein.

The circulating PCSK9 binds to the EGF-A domain of LDLR and promotes degradation of the LDLR. The hepatic LDLR is the primary pathway for elimination of LDLc from plasma. Circulating LDLc binds to the LDLR and formed complex which is internalized by receptor-mediated endocytosis. Subsequently, LDLc is preceded for degradation and LDLR is recycled back to the cell surface. The PCSK9 interact with the LDLR and this PCSK9-LDLR interaction causes the degradation of LDLR, reducing the LDLR availability for the clearance of LDLc from plasma. This clearly specifies the significance of PCSK9 as a regulator of LDLR and in LDLc metabolism.

Several approaches such as monoclonal antibodies (mAbs), PCSK9 inhibition using small interfering RNA (siRNA), antisense oligonucleotides, PCSK9-binding adnectins, small molecule inhibitors and inhibitors of autocatalysis were attempted to reduce the amount of circulating PCSK9 or inhibiting its interaction with the LDLR. However, PCSK9 acts intracellularly and extracellularly on LDLR, targeting circulating PCSK9 is a valuable approach for lowering LDLc levels. The encouraging results from human clinical trials with PCSK9-specific mAbs indicate that targeting PCSK9 permits efficient and safe LDLc reduction. Moreover, several clinical trials to evaluate the safety and efficacy of targeting PCSK9 were recently successfully completed. In conclusion, apart from statins, identification of PCSK9 as alternative target to control LDLc levels is of great significance.

In addition to several approaches by various organisations to inhibit the LDLR degradation mediated through circulating PCSK9, recently, Pfizer (WO2011027257A2) and Affiris (WO2014033158A2) through its multiple patents disclosed antigenic peptides which were able to induce the antibodies that specifically bind to human PCSK9 and inhibit the PCSK9-mediated degradation of LDLR.

Since the finding of PCSK9 gene and its role in cholesterol reduction, several approaches were tested to inhibit the PCSK9-mediated degradation of LDLR. Currently monoclonal antibodies (mAbs) targeting PCSK9 were evaluated for use in human. Recently, Regeneron/Sanofi have developed Alirocumab (mAbs) and published several patent applications such as WO/2015/140079, (EP2015/055369), WO/2015/142668 (US2015/020564) & WO/2015/123423 (US2015/015633) WO/2014/194111, (US2014/040050), WO/2014/194168 (US2014/040163), WO/2013/039969 (US2012/054756) which covers an anti-PCSK9 antibody such as mAb316P were approved for human use. In addition to this, Sanofi WO/2015/073494 (US2014/065149), WO/2015/054619, (US2014/060109), & Regeneron Pharmaceuticals WO/2014/197752 (US2014/041204) also discloses PCSK9 inhibitor which are anti-PCSK9 antibody, or antigen binding protein. Further Sanofi WO/2012/101251 (EP2012/051318), WO/2012/101253 (EP2012/051321), WO/2012/101252 (EP2012/051320) have developed PCSK9-specific antibodies or antigen-binding fragments and preferably by additional administration of a HMG-CoA reductase inhibitor.

Evolocumab (AMG-145) developed by Amgen is fully human mAbs, or antigen binding proteins capable of inhibiting PCSK9 binding to LDLR approved for human use [WO/2014/209384 (US2013/048714), WO/2014/150983 (US2014/024702), WO/2014/144080 (US2014/028339), WO/2013/166448 (US2013/039561), WO/2012/154999 (US2012/037394)]. While Bococizumab, a humanized mAb developed by Pfizer, [WO/2013/008185 (IB2012/053534)] is under investigation. Eli Lilly [LY3015014] is developing another PCSK9 mAb currently undergoing phase II trials [WO/2013/039958 (US2012/054737)].

Several other PCSK9 antagonist antibodies have been developed by Eleven Biotherapeutics WO/2015/200438 (US2015/037345), WO/2014/107739 (US2014/010536), Genentech, WO/2013/188855 (US2013/046032), WO/2012/088313 (US2011/066593); Alderbio Holdings WO/2013/169886 (US2013/040112); Adaerata WO/2013/091103 (CA2012/050923); Novartis WO/2012/168491 (EP2012/061045), WO/2012/170607 (US2012/041214); IRM LLC WO/2012/109530 (US2012/024633), WO/2011/072263 (US2010/059959); and Merck Sharp & Dohme Corp WO/2012/054438 (US2011/056649), WO/2011/053759 (US2010/054640), WO/2011/053783, (US2010/054714), WO/2011/037791 (US2010/048849), many of which are under investigation.

In another approach, the inhibition of PCSK9 expression using RNA interference (RNAi) is been used. Several companies including Roche WO/2014/207232 (EP2014/

063757); Pfizer WO/2014/170786 (IB2014/060407); Alnylam Pharmaceuticals WO/2014/089313 (US2013/073349), WO/2012/058693 (US2011/058682) WO/2011/038031 (US2010/049868), WO/2011/028938 (US2010/047726); Kowa Company LTD WO/2014/017569 (JP2013/070128); Osaka University WO/2014/007305 (JP2013/068299), WO/2012/029870 (JP2011/069818); New York University WO/2013/154766 (US2013/032271) and Santaris Pharma WO/2011/009697 (EP2010/059257) are developing PCSK9 expression inhibitors using RNAi and many of these are in various stages of clinical development.

An anti-PCSK9 active vaccination strategy is an alternate strategy to inhibit PCSK9. Patent applications by Pfizer WO/2012/131504 (IB2012/050924), The Secretary, Dept. of Health and Human services USA, WO/2015/123291 (US2015/015408), and Istituto di Ricerche di Biologia Molecolare WO/2011/117401 (EP2011/054646) discloses various vaccination strategies to lower down the LDLc level.

Another promising approach is the peptide-based PCSK9 vaccines for PCSK9 inhibition. The short chain peptides derived from the PCSK9 gene are conjugated with suitable immunogenic carriers which are capable of producing antibodies against the PCSK9. Patent applications by Pfizer (WO/2011/027257 (IB2010/053784), US2011/0052621; Affiris US2016/0106822, WO/2015/128287 (EP2015/053725), EP2703483, WO/2014/033158 (EP2013/067797), WO/2013/037889 (EP2012/067950) discloses such immunogenic peptides in controlling the LDLc level.

However, so far, no PCSK9 peptide vaccines containing unnatural/modified amino acids have been reported and also no significant attempts have been made to improve the metabolic stability of these PCSK9 peptides, using suitable chemical modifications so as to improve its efficacy and/or potency along with duration of action. The present invention is one of the first attempts to investigate the role of modified amino acid incorporated in PCSK9 peptide from PCSK9 gene which are then conjugated with suitable immunogenic carrier. Surprisingly, many of these modified peptides have been found to be capable to induce the formation of antibodies directed to PCSK9. These vaccines can therefore be useful in the treatment or prevention of diseases mediating through PCSK9.

The aim of the present invention is to provide certain novel short-chain peptides Formula (I) which may be conjugated with suitable immunogenic carrier and capable of producing antibodies that specifically bind to human PCSK9 and inhibit the PCSK9-mediated degradation of LDLR. The objective was achieved by developing certain modified peptides by replacing the natural amino acids by unnatural amino acids optionally conjugated with a suitable immunogenic carrier and evaluated for the production of antibodies specifically directed towards the PCSK9 gene, thereby reducing the levels of LDLc which can be used for the treatment of cardiovascular complications like hyperlipidaemia, hypercholesterolemia, or atherosclerosis.

Thus, the present invention relates to novel short-chain peptides of Formula (I), which are optionally conjugated with suitable immunogenic carrier. Such compositions can be used as a vaccine or a vaccine composition. In a preferred embodiment, the peptide comprises of 12 amino acid residues of Formula (I), $$A\text{-}Z_1\text{-}Z_2\text{-}Z_3\text{-}Z_4\text{-}Z_5\text{-}Z_6\text{-}Z_7\text{-}Z_8\text{-}Z_9\text{-}Z_{10}\text{-}Z_{11}\text{-}Z_{12}\text{-}B \qquad \text{Formula (I)}$$

Wherein,

'A' represents the groups —NH—$R_1$, $R_2$—CO—NH—, wherein '$R_1$' represents hydrogen or optionally substituted linear or branched ($C_{1-18}$) alkyl chain; '$R_2$' is selected from optionally substituted linear or branched ($C_{1-18}$) alkyl chain, ($C_{1-6}$)alkoxy, ($C_3$-$C_6$) cycloalkyl, aryl, heteroaryl or arylalkyl groups;

In a preferred embodiment, the aryl group is selected from phenyl, naphthyl, indanyl, fluorenyl or biphenyl, groups; the heteroaryl group is selected from pyridyl, thienyl, furyl, imidazolyl, benzofuranyl groups;

'B' represents $R_3$, —$COOR_3$, —$CONHR_3$ or $CH_2OR_3$, wherein $R_3$ represents H or suitable amino acids such as serine, cysteine, valine, alpha-methyl-valine, Lys(Biotin), Lys(alkyl), Lys(acetyl) and the like;

$Z_1$ is an amino acid residue selected from the group of uncharged amino acid residues, preferably selected from the group of serine, threonine, valine and alanine and their derivatives such as homoserine, O-methyl-threonine, O-methyl-serine, O-methyl-homoserine, etc.

$Z_2$ is an amino acid residue selected from the group of uncharged amino acid residues, preferably selected from the group of isoleucine, leucine, norleucine, glycine, alanine, Aib and their derivatives such as N-methyl-isoleucine, N-methyl-leucine, etc.

$Z_3$ is an amino acid residue selected from the group of proline, 1-amino carbocyclic acids and their derivatives such as hydroxyproline, thiaproline, aminoproline, alpha-methyl-proline, 3-fluoroproline, 4-fluoroproline, 1-amino-cyclopropanecarboxylic acid, 1-amino-cyclopentanecarboxylic acid, 1-amino-cyclohexanecarboxylic acid, etc.

$Z_4$ is an amino acid residue selected from the group of tryptophan, phenylalanine, tyrosine and their derivatives;

$Z_5$ is an amino acid residue selected from the group of glutamine, histidine, preferably aspargine and their derivatives;

$Z_6$ is an amino acid residue selected from the group of uncharged amino acid residues, preferably selected from the group of isoleucine, leucine, alanine, threonine, aspartic acid, Aib and their derivatives such as norisoleucine, N-methyl-leucine homoleucine, alpha-methyl-aspartic acid, etc.

$Z_7$ is an amino acid residue selected from the group of hydrophilic, negatively charged amino acid residue, preferably an amino acid residue selected from the group of glutamic acid, aspartic acid and their derivatives such as alpha-methyl-aspartic acid, alpha-methyl-glutamic acid, homoglutamic acid etc.

$Z_8$ is an amino acid residue selected from the group of amino acid residues, preferably selected from the group of arginine, homoarginine, citruline, glutamine, aspargine, lysine and their derivatives;

$Z_9$ is an amino acid residue selected from the group of uncharged amino acid residues, preferably selected from the group of isoleucine, leucine, norleucine, glycine, alanine or Aib and their derivatives such as N-methyl isoleucine, etc.

$Z_{10}$ is an amino acid residue selected from the group of polar and uncharged amino acid residues, preferably selected from the group of serine, threonine, valine, alanine and their derivatives;

$Z_{11}$ is any amino acid residue, preferably an amino acid residue selected from the group of amino acid residues, preferably selected from the group of proline, and their derivatives such as hydroxyproline, thiaproline, alpha-methyl-proline, 3-fluoroproline, 4-fluoroproline, 1-amino-cyclopropanecarboxylic acid, 1-amino-cyclopentanecarboxylic acid, 1-amino-cyclohexanecarboxylic acid, etc.

$Z_{12}$ is any amino acid residue, preferably polar and uncharged amino acid residue selected from the group of cysteine, homocysteine and their derivatives; with the proviso that at least one of $Z_1$ to $Z_{12}$ always represents an unnatural amino acid.

Single-letter abbreviations for amino acids used in the present invention can be found in Zubay, G., Biochemistry $2^{nd}$ ed., 1988, MacMillan Publishing, New York, p. 33.

A series of PCSK9 peptides are reported herein with general formula A-$Z_1$-$Z_2$-$Z_3$-$Z_4$-$Z_5$-$Z_6$-$Z_7$-$Z_8$-$Z_9$-$Z_{10}$-$Z_{11}$-$Z_{12}$-B (I), wherein each of $Z_1$-$Z_{12}$ when present, represents the naturally occurring amino acid or unnatural/modified amino acids sequences, with the proviso that at least one of $Z_1$-$Z_{12}$ will always represent an unnatural/modified amino acid.

SUMMARY OF THE INVENTION

The present invention provides novel short-chain PCSK9 peptide sequence optionally conjugated with a suitable immunogenic carrier and are capable to inhibit the PCSK9 mediated degradation of the LDLR. These peptides are suitably modified with unnatural amino acids and conjugated with suitable immunogenic carrier so as to improve its immunogenic potency and thereby increasing the antibodies production. These short chain peptides here onward called as PCSK9 peptide derivatives/analogue are mainly derived from the active peptide sequence of human PCSK9 gene. These novel immunogenic short-chain PCSK9 peptide analogue based vaccines are useful for the treatment or prevention of pathology associated with the regulation of plasma LDL-c level. The antibody produced by these vaccines prevents PCSK9 mediated degradation of the LDLR, thereby controlling the health disorders like hyperlipidaemia, hypercholesterolemia, or atherosclerosis.

PREFERRED EMBODIMENTS

An embodiment of the present invention is to provide novel short-chain peptides of general formula (I), novel intermediates involved in their synthesis, their pharmaceutically acceptable salts and pharmaceutical compositions containing them or their mixtures suitable as vaccines against PCSK9 gene.

In another embodiment, the short chain peptides of formula (I) are conjugated with suitable immunogenic carrier to act as vaccines which are able to induce the formation of antibodies which bind specifically to PCSK9 in living systems. The interaction of the antibodies with PCSK9 inhibits LDLR degradation and causes reduction of the plasma LDLc levels. These vaccines can be suitable for the treatment of health disorders like hyperlipidaemia, hypercholesterolemia, or atherosclerosis.

In a further preferred embodiment, is provided pharmaceutical compositions containing short-chain peptides of general formula (I), their pharmaceutically acceptable salts, solvates and their mixtures in combination with pharmaceutically acceptable adjuvants, immunogenic carriers, solvents, diluents, excipients and other media normally employed in their manufacture.

In yet another preferred embodiment, is provided pharmaceutical compositions containing short-chain peptides of general formula (I), conjugated with suitable immunogenic carriers in combination with suitable solvents, diluents, other excipients and other media normally employed in their manufacture.

In a still further preferred embodiment is provided the use of the novel short-chain peptides of formula (I) alone or when conjugated with suitable immunogenic carrier for the treatment of health disorders like hyperlipidaemia, hypercholesterolemia, or atherosclerosis and other cardiovascular diseases.

According to a particularly preferred embodiment the novel short-chain peptides in the vaccine of the present invention contains at its N- and/or C-terminus at least one cysteine residue bound directly or via a spacer sequence. This cysteine residue serves as a reactive group in order to bind the peptide to another molecule or a carrier protein.

In the further preferred embodiment of the present invention the immunogenic carrier is selected from the group consisting of diphtheria toxin (DT), keyhole limpet haemocyanin (KLH), CRM (preferably CRM197), tetanus toxoid (TT), protein D or any other protein or peptide containing helper T-cell epitopes.

In a further preferred embodiment the adjuvant is selected from alum, alum in combination with MF-59, TLR3 agonist such as Poly(I:C), TLR 4 agonist such as Monophosphoryl Lipid A or GLA and like, TLR5 agonist such as Flagellin, TLR7 agonist such as Gardiquimod and Imiquimod TLR7/8 agonist such as R848, NOD2 agonist such as N-glycolyl-MDP.CpG-containing nucleic acid (where the cytosine is unmethylated), QS21 (saponin adjuvant), interleukins, beta-sitosterol and the like.

In a further preferred embodiment the adjuvant is selected from alum, alum in combination with other adjuvants like MF-59, GLA, Monophosphoryl Lipid A, CpG-containing nucleic acid (where the cytosine is unmethylated), QS21 (saponin adjuvant), interleukins, beta-sitosterol.

ABBREVIATIONS USED

The following abbreviations are employed in the examples and elsewhere herein:
Ac=Acetyl
Aib=α-Amino-isobutyric acid,
Abu(CN)=2-amino-4-cyanobutanoic acid,
A-Me-APPA=alpha-methyl-2-aminophenyl pentanoic acid,
α-Me-Asp=alpha-methyl-aspartic acid
α-Me-D=alpha-methyl-aspartic acid,
α-Me-E or αMe-Glu=alpha-methyl-glutamic acid,
α-Me-L=alpha-methyl-leucine,
α-Me-Phe=alpha-methyl-phenylalanine,
α-Me-2F-Phe=alpha-methyl-2-fluorophenylalanine,
α-Me-2,6-diF-Phe=alpha-methyl-2,6-diflurophenylalanine,
α-Me-Pro=alpha-methyl-proline,
$AC_3C$=1-amino-cyclopropanecarboxylic acid,
$AC_5C$=1-amino-cyclopentanecarboxylic acid,
$AC_6C$=1-amino-cyclohexanecarboxylic acid,
ACN=Acetonitrile,
APPA=2-Aminophenyl pentanoic acid,
Amp=4-Aminoproline,
3-Amp=3-Aminoproline,
B-Ala=beta alanine,
Boc=tert-Butoxycarbonyl,
$Bu^t$=O-tert-butyl group,
Cit=Citrulline
DCM=Dichloromethane,
DMF=N,N-Dimethylformamide,
DIPCDI=Di-isopropylcarbodiimide,
DIPEA=Diisopropylethylamine,
Et=Ethyl,
$Et_2O$=Diethyl ether,
2F-Phe=2-fluorophenylalanine,
3F-Pro=3-fluoroproline,
4F-Pro=4-fluoroproline,
Fmoc=Fluorenylmethoxycarbonyl, g=Gram (s),
h=Hour (s),
Har=homoarginine
HoGlu or Homo-Glu=homoglutamic acid,
HoLeu=homoleucine,
HoSer=homoserine,
Hyp=4-Hydroxyproline,
3-Hyp=3-Hydroxyproline,
HOBt=1-Hydroxybenzotriazole,
HOAt=7-Aza-hydroxybenzotriazole,
HBTU=2-(1H-benzotriazole-1-yl)-1,1,3,3-tetramethyl aminium hexafluorophosphate,
HPLC=High Performance Liquid Chromatography,
K(Biotin)=Lysine(Biotin),
L=Liter,
LC/MS=Liquid Chromatography/Mass Spectrometry,
Me=Methyl,
Min=minute (s),
mL=milliliter,
μl=microliter,
mg=milligram (s),
mmol=millimole (s),
MS=Mass Spectrometry,
Nle=Norleucine,
NMe-Ile=N-methyl-isoleucine
NMe-Leu=N-methyl-leucine
NMe-Nle=N-methyl-norleucine
OMe-Thr or Thr(OMe)=O-methyl-threonine,
OMe-Ser or Ser(OMe)=O-methyl-serine,
OMe-HoSer or HoSer(OMe)=O-methyl-homoserine,
PyBOP=Benzotriazole-1-yl-oxy-tris-pyrrolidino-phosphonium hexafluorophosphate,
2-Pal=2-Pyridylalanine,
Pal=3-Pyridylalanine,
4-Pal=4-Pyridylalanine,
Sar=Sarcosine,
SPPS=Solid Phase Peptide Synthesis,
2-Thi=(2-Thienyl)-alanine,
Tha=(4-Thiazolyl)-alanine,
Thz=4-Thiaproline,
2-Thz=2-Thiaproline,
TMS=Trimethylsilyl,
TIPS=Triisopropylsilane,
TFA=Trifluoroacetic acid,
TBTU=2-(1H-benzotriazole-1-yl)-1,1,3,3-tetramethylaminium tetrafluoroborate,
Trt=Trityl group.

DETAILED DESCRIPTION OF THE INVENTION

In accordance with the present invention, the various novel short-chain peptides having the structural Formula (I), were synthesised and then conjugated with a suitable immunogenic carrier. These vaccines can be used for the treatment of health disorders like hyperlipidemia, hypercholesterolemia, or atherosclerosis.

In one aspect, the present invention thus discloses PCSK9 peptide derivatives having following structure of Formula (I)

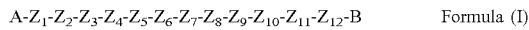

A-$Z_1$-$Z_2$-$Z_3$-$Z_4$-$Z_5$-$Z_6$-$Z_7$-$Z_8$-$Z_9$-$Z_{10}$-$Z_{11}$-$Z_{12}$-B     Formula (I)

Wherein,

'A' represents the groups —NH—$R_1$, $R_2$—CO—NH—, wherein '$R_1$' represents hydrogen or optionally substituted linear or branched ($C_{1-18}$) alkyl chain; '$R_2$' is selected from optionally substituted linear or branched ($C_{1-18}$) alkyl chain, ($C_{1-6}$)alkoxy, ($C_3$-$C_6$) cycloalkyl, aryl, heteroaryl or arylalkyl groups;

wherein aryl group is selected from phenyl, naphthyl, indanyl, fluorenyl or biphenyl, groups; the heteroaryl group is selected from pyridyl, thienyl, furyl, imidazolyl, benzofuranyl groups;

'B' represents $R_3$, —COO$R_3$, —CONH$R_3$ or $CH_2OR_3$, wherein $R_3$ represents H or suitable amino acids such as serine, cysteine, valine, alpha-methyl-Valine, Lys(Biotin), Lys(alkyl), Lys(acetyl) and the like;

$Z_1$ is an amino acid residue selected from the group of uncharged amino acid residues, preferably selected from the group of serine, threonine, valine and alanine and their derivatives such as homoserine, O-methyl-threonine, O-methyl-serine, O-methyl-homoserine, etc.

$Z_2$ is an amino acid residue selected from the group of uncharged amino acid residues, preferably selected from the group of isoleucine, leucine, norleucine, glycine, alanine, Aib and their derivatives such as N-methyl-isoleucine and N-methyl-leucine, etc.

$Z_3$ is an amino acid residue selected from the group of proline, 1-amino carbocyclic acids and their derivatives such as hydroxyproline, thiaproline, aminoproline, alpha-methyl-proline, 3-fluoroproline, 4-fluoroproline, 1-amino-cyclopropanecarboxylic acid, 1-amino-cyclopentanecarboxylic acid, 1-amino-cyclohexanecarboxylic acid, etc.

$Z_4$ is an amino acid residue selected from the group preferably of tryptophan, phenylalanine, tyrosine and their derivatives;

$Z_5$ is an amino acid residue selected from the group of glutamine, histidine, preferably aspargine and their derivatives;

$Z_6$ is an amino acid residue selected from the group of uncharged amino acid residues, preferably selected from the group of isoleucine, leucine, alanine, threonine, aspartic acid, Aib and their derivatives such as norisoleucine, N-methyl-leucine homoleucine, alpha-methyl-aspartic acid, etc.

$Z_7$ is an amino acid residue selected from the group of hydrophilic, negatively charged amino acid residue, preferably an amino acid residue selected from the group of glutamic acid, aspartic acid and their derivatives such as alpha-methyl-aspartic acid, alpha-methyl-glutamic acid, homoglutamic acid etc.

$Z_8$ is an amino acid residue selected from the group of amino acid residues, preferably selected from the group of arginine, homoarginine, citruline, glutamine, aspargine, lysine and their derivatives;

$Z_9$ is an amino acid residue selected from the group of uncharged amino acid residues, preferably selected from the group of isoleucine, leucine, norleucine, glycine, alanine, Aib and their derivatives such as N-methyl isoleucine, etc.

$Z_{10}$ is an amino acid residue selected from the group of polar and uncharged amino acid residues, preferably selected from the group of serine, threonine, valine, alanine and their derivatives;

$Z_{11}$ is any amino acid residue, preferably an amino acid residue selected from the group of amino acid residues, preferably selected from the group of proline, and their derivatives such as hydroxyproline, thiaproline, or alpha-methyl-proline, 3-fluoroproline, 4-fluoroproline, 1-amino-cyclopropanecarboxylic acid, 1-amino-cyclopentanecarboxylic acid, 1-amino-cyclohexanecarboxylic acid etc.

$Z_{12}$ is any amino acid residue, preferably polar and uncharged amino acid residue selected from the group of cysteine, homocysteine and their derivatives; with the proviso that at least one of $Z_1$ to $Z_{12}$ always represents an unnatural amino acid.

In one of the preferred embodiments, 'A' represents the groups —NH—$R_1$, $R_2$—CO—NH—, wherein '$R_1$' is hydrogen or substituted linear or branched ($C_{1-18}$) alkyl chain; '$R_2$' is selected from substituted linear or branched ($C_{1-18}$) alkyl chain, ($C_{1-6}$) alkoxy, ($C_3$-$C_6$) cycloalkyl, aryl, and arylalkyl groups; wherein the aryl group is selected from phenyl, naphthyl, indanyl, fluorenyl or biphenyl, groups; 'B' represents $R_3$, —COO$R_3$, —CONH$R_3$ or $CH_2OR_3$, wherein $R_3$ is selected from H, serine, cysteine, valine, alpha-methyl-valine, Lys(Biotin), Lys(alkyl), Lys(acetyl), $Z_1$ is selected from serine, threonine, valine, alanine, Aib, homoserine, O-methyl-threonine, O-methyl-serine or O-methyl-homoserine, $Z_2$ is selected from isoleucine, leucine, norleucine, glycine, alanine, Aib, N-methyl-isoleucine or N-methyl-leucine, $Z_3$ is selected from proline, hydroxyproline, thiaproline, aminoproline, 2-thiaproline, 3-hydroxyproline, 3-aminoproline, alpha-methyl-proline, 3-fluoroproline, 4-fluoroproline, 1-amino-cyclopropanecarboxylic acid, 1-amino-cyclopentanecarboxylic acid or 1-amino-cyclohexanecarboxylic acid, $Z_4$ is selected from tryptophan, phenylalanine, tyrosine, 2-fluorophenylalanine, alpha-methyl phenylalanine, alpha-methyl-2-fluorophenylalanine, alpha-methyl-2,6-difluorophenylalanine, 2-amino-5-phenyl-pentanoic acid, alpha-methyl-2-amino-5-phenyl-pentanoic acid or 2'-ethyl-4'-methoxy-biphenylalanine, $Z_5$ is selected from glutamine, histidine or aspargine, $Z_6$ is selected from isoleucine, leucine, alanine, threonine, aspartic acid, Aib, norisoleucine, N-methyl-leucine, homoleucine, beta-alanine or alpha-methyl-aspartic acid, $Z_7$ is glutamic acid, aspartic acid, alpha-methyl-aspartic acid, alpha-methyl-glutamic acid, 2-amino-4-cyanobutanoic acid or homoglutamic acid, $Z_8$ is selected from arginine, homoarginine, citruline, glutamine, aspargine or lysine, $Z_9$ is selected from isoleucine, leucine, norleucine, glycine, alanine, Aib or N-methyl isoleucine, $Z_{10}$ is selected from serine, threonine, valine, Aib or alanine, $Z_{11}$ is selected from proline, hydroxyproline, thiaproline, aminoproline, alpha-methyl-proline, 3-fluoroproline, 4-fluoroproline, 1-amino-cyclopropanecarboxylic acid, 1-amino-cyclopentanecarboxylic acid or 1-amino-cyclohexanecarboxylic acid, $Z_{12}$ is selected from cysteine or Homocysteine.

Definitions

The term 'natural amino acids' indicates all those twenty amino acids, which are present in nature. The term 'unnatural amino acids' or 'non-natural amino acids' preferably represents either replacement of L-amino acids with corresponding D-amino acids such as replacement of L-Ala with D-Ala and the like or suitable modifications of the L or D amino acids, amino alkyl acids, either by α-alkylation such as substitution of Ala with α-methyl Ala (Aib), replacement of Leu with α-methyl Leu;

substitution on the side chain of amino acid such as substitution of aromatic amino acid side chain with halogen, ($C_1$-$C_3$) alkyl, aryl groups, more specifically the replacement of Phe with halo Phe;

β amino acids such as β alanine;

The various groups, radicals and substituents used anywhere in the specification are described in the following paragraphs.

The term "alkyl" used herein, either alone or in combination with other radicals, denotes a linear or branched radical containing one to eighteen carbons, such as methyl, ethyl, n-propyl, iso-propyl, n-butyl, sec-butyl, tert-butyl, amyl, t-amyl, n-pentyl, n-hexyl, iso-hexyl, heptyl, octyl, decyl, tetradecyl, octadecyl and the like.

The term "cycloalkyl" used herein, either alone or in combination with other radicals, denotes a radical containing three to seven carbons, such as cyclopropyl, cyclobutyl, cyclopentyl, cyclohexyl, cycloheptyl and the like.

Unless otherwise indicated, the term 'amino acid' as employed herein alone or as part of another group includes, without limitation, an amino group and a carboxyl group linked to the same carbon, referred to as 'α' carbon.

The absolute 'S' configuration at the 'α' carbon is commonly referred to as the 'L' or natural configuration. The 'R' configuration at the 'α' carbon is commonly referred to as the 'D' amino acid. In the case where both the 'α-substituents' is equal, such as hydrogen or methyl, the amino acids are Gly or Aib and are not chiral.

The term 'derivatives' mentioned anywhere in document indicates any substituted or homologous non-natural amino acid of that particular amino acid.

While the invention has been primarily exemplified in relation to short chain peptides, it will also be understood that the peptide linkage between the residues may be replaced by a non-peptide bond provided that the therapeutic potential is retained. The person skilled in the art will be aware of suitable modifications, such as thioamide bond formation, N-methylation of amide bonds and the like.

Sequences encompassing conservative substitutions of amino acids are also within the scope of the invention, provided that the biological activity is retained.

It is to be clearly understood that the compounds of the invention include peptide amides and non-amides and peptide analogues, including but not limited to the following:

a) Compounds in which one or more amino acids is replaced by its corresponding D-amino acid. The skilled person will be aware that retro-inverso amino acid sequences can be synthesized by standard methods; see for example, Chorev M., Acc. Chem. Res., 26, 1993, 266-273;

b) Compounds, in which the peptide bond is replaced by a structure more resistant to metabolic degradation. See for example, Olson G. L., et al., J. Med. Chem., 36(21), 1993, 3039-3049 and c) Compounds in which individual amino acids are replaced by analogous structures for example Ala with Aib; Arg with Cit.

Throughout the description the conventional one-letter and three-letter code for natural amino acids are used as well as generally acceptable three-letter codes for other unnatural amino acids such as Hyp (Hydroxyproline), Thz (Thiaproline), Aib (α-amino isobutanoic acid) are used.

Preparation of the Short Chain Peptides:

Several synthetic routes can be employed to prepare the short chain peptides of the present invention well known to one skilled in the art of peptide synthesis. The short chain peptides of formula (I), where all symbols are as defined earlier can be synthesized using the methods described below, together with conventional techniques known to those skilled in the art of peptide synthesis, or variations thereon as appreciated by those skilled in the art. Referred methods include, but not limited to those described below.

The short chain peptides thereof described herein may be produced by chemical synthesis using suitable variations of both the solution-phase (preferably, using Boc-chemistry; M. Bodansky, A. Bodansky, "The practice of peptide synthesis", Springer-Verlag, Berlin, 1984; E. Gross, J. Meinhofer, "The peptide synthesis, analysis, biology", Vol. 1, Academic Press, London, 1979) and or solid-phase techniques, such as those described in G. Barany & R. B. Merrifield, "The peptides: Analysis, synthesis, Biology"; Volume 2—"Special methods in peptide synthesis, Part A", pp. 3-284, E. Gross & J. Meienhofer, Eds., Academic Press, New York, 1980; and in J. M. Stewart and J. D. Young, "Solid-phase peptide synthesis" 2nd Ed., Pierce chemical Co., Rockford, Ill., 1984.

The preferred strategy for preparing the short chain peptides of this invention is based on the use of Fmoc-based SPPS approach, wherein Fmoc (9-fluorenylmethoxycarbonyl) group is used for temporary protection of the α-amino group, in combination with the acid labile protecting groups, such as tert-butoxycarbonyl (Boc), tert-butyl (Bu$^t$), Trityl (Trt) groups (Figure 1), for temporary protection of the amino acid side chains, if present (see for example E. Atherton & R. C. Sheppard, "The Fluorenylmethoxycarbonyl amino protecting group", in "The peptides: Analysis, synthesis, Biology"; Volume 9—"Special methods in peptide synthesis, Part C", pp. 1-38, S. Undenfriend & J. Meienhofer, Eds., Academic Press, San Diego, 1987).

The short chain peptides can be synthesized in a stepwise manner on an insoluble polymer support (resin), starting from the C-terminus of the peptide. In an embodiment, the synthesis is initiated by appending the C-terminal amino acid of the peptide to the resin through formation of an amide, ester or ether linkage. This allows the eventual release of the resulting peptide as a C-terminal amide, carboxylic acid or alcohol, respectively.

In the Fmoc-based SPPS, the C-terminal amino acid and all other amino acids used in the synthesis are required to have their α-amino groups and side chain functionalities (if present) differentially protected (orthogonal protection), such that the α-amino protecting group may be selectively removed during the synthesis, using suitable base such as 20% piperidine solution, without any premature cleavage of peptide from resin or deprotection of side chain protecting groups, usually protected with the acid labile protecting groups.

The coupling of an amino acid is performed by activation of its carboxyl group as an active ester and reaction thereof with unblocked α-amino group of the N-terminal amino acid appended to the resin. After every coupling and deprotection, peptidyl-resin was washed with the excess of solvents, such as DMF, DCM and diethyl ether. The sequence of α-amino group deprotection and coupling is repeated until the desired peptide sequence is assembled (Scheme 1). The peptide is then cleaved from the resin with concomitant deprotection of the side chain functionalities, using an appropriate cleavage mixture, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.). Preferred for use in this invention is Fmoc-PAL-PEG-PS resin, 4-(2',4'-dimethoxyphenyl-Fmoc-aminomethyl)-phenoxyacetyl-p-methyl benzhydrylamine resin (Fmoc-Rink amide MBHA resin), 2-chloro-Trityl-chloride resin or p-benzyloxybenzyl alcohol resin (HMP resin) to which the C-terminal amino acid may or may not be already attached. If the C-terminal amino acid is not attached, its attachment may be achieved by HOBt active ester of the Fmoc-protected amino acid formed by its reaction with DIPCDI. In case of 2-Chloro-trityl resin, coupling of first Fmoc-protected amino acid was achieved, using DIPEA. For the assembly of next amino acid, N-terminal protection of peptidyl resin was selectively deprotected using 10-20% piperidine solution. After every coupling and deprotection, excess of amino acids and coupling reagents were removed by washing with DMF, DCM and ether. Coupling of the subsequent amino acids can be accomplished using HOBt or HOAT active esters produced from DIPCDI/HOBt or DIPCDI/HOAT, respectively. In case of some difficult coupling, especially coupling of those amino acids, which are hydrophobic or amino acids with bulky side chain protection; complete coupling can be achieved using a combination of highly efficient coupling agents such as HBTU, PyBOP or TBTU, with additives such as DIPEA.

The synthesis of the short chain peptides described herein can be carried out by using batchwise or continuous flow peptide synthesis apparatus, such as CS-Bio or AAPPTEC peptide synthesizer, utilizing the Fmoc/t-butyl protection strategy. The non-natural non-commercial amino acids present at different position were incorporated into the peptide chain, using one or more methods known in the art. In one approach, Fmoc-protected non-natural amino acid was prepared in solution, using appropriate literature procedures. For example, the Fmoc-protected APPA analogs, described above, were prepared from L-pyroglutamic acid, in good enantiomeric purity, using modified literature procedure (Betsbrugge J. V., et al., Tetrahedron, 54, 1988, 1753-1762).

Figure 1: Examples of some of the protected amino acids used in Fmoc based-Solid Phase Peptide Synthesis (SPPS) of short chain peptides.

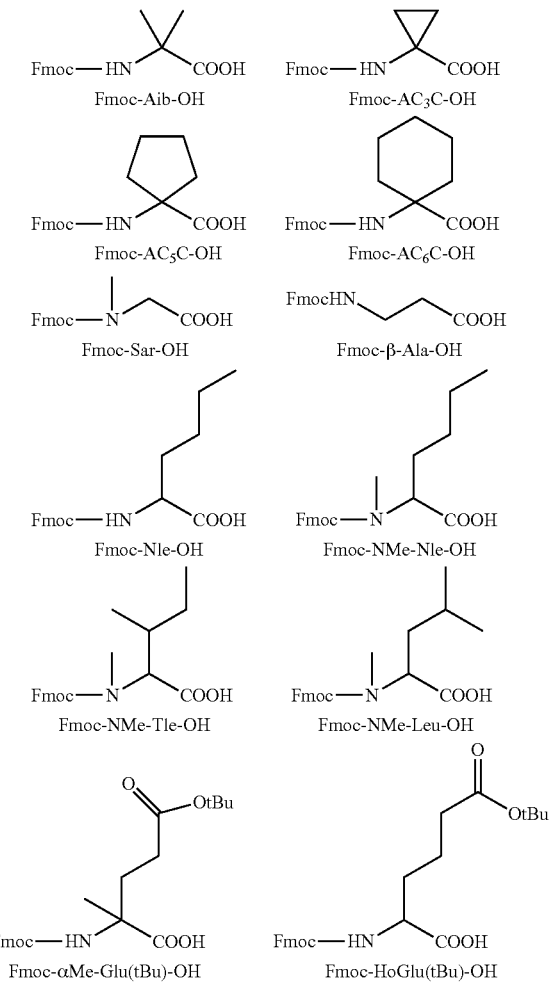

-continued

Fmoc-αMe-Asp(tBu)-OH
Fmoc-HoLeu-OH
Fmoc-αMe-Leu-OH
Fmoc-Abu(CN)-OH
Fmoc-αMe-Pro-OH
Fmoc-Thz-OH
Fmoc-2-Thz-OH
Fmoc-Hyp(tBu)-OH
Fmoc-3-Hyp(tBu)-OH
Fmoc-Amp(Boc)-OH
Fmoc-3-Amp(Boc)-OH
Fmoc-4F-Pro-OH
Fmoc-3F-Pro-OH
Fmoc-Arg(NO)$_2$-OH
Fmoc-Cit-OH -continued Fmoc-Har-OH
Fmoc-HoCit-OH
Fmoc-Orn-OH
Fmoc-Ser(OMe)-OH
Fmoc-HoSer(tBu)-OH
Fmoc-Thr(OMe)-OH
Fmoc-HoSer(OMe)-OH
Fmoc-2F-Phe-OH
Fmoc-(αMe-Phe)-OH
Fmoc-(αMe-2F-Phe)-OH
Fmoc-(αMe-2,6-F-Phe)-OH
Fmoc-APPA-OH

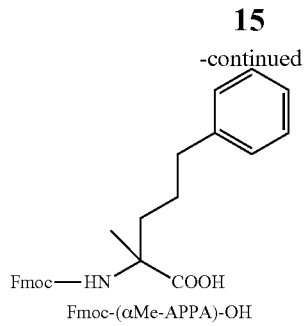

Fmoc-(αMe-APPA)-OH

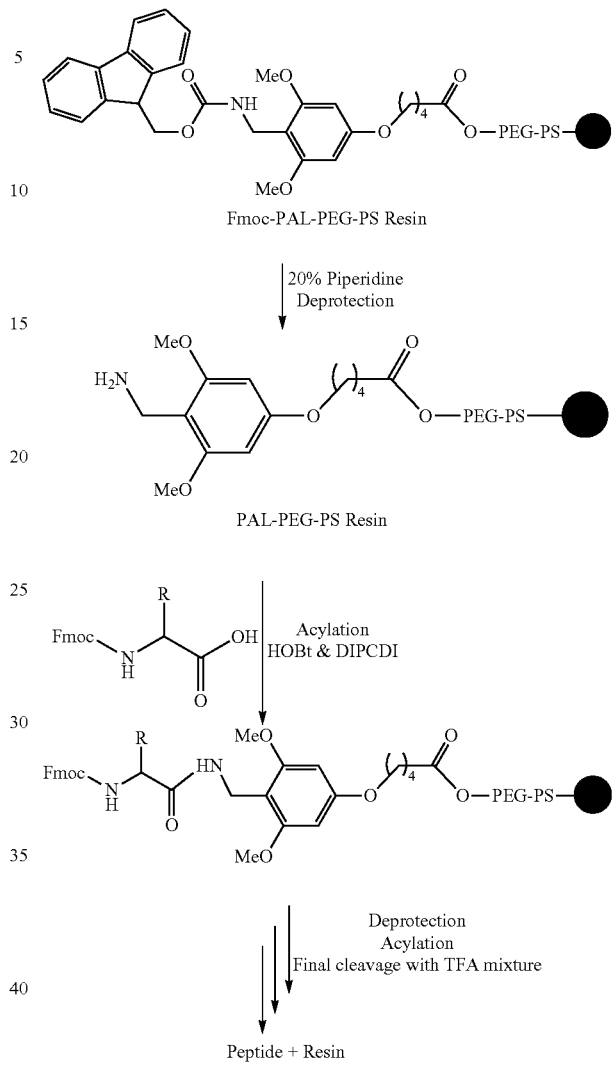

Scheme 1: General Scheme for Fmoc-Based SPPS

The Fmoc-protected α-methylated amino acids were prepared using asymmetric Strecker synthesis (Boesten, W. H. J., et al., Org. Lett., 3(8), 2001, 1121-1124; Cativiela C., Diaz-de-villegas M. D., Tetrahedran Asymmetry, 9, 1988, 3517-3599). The resulting derivative was then used in the step-wise synthesis of the peptide. Alternatively, the required non-natural amino acid was built on the resin directly using synthetic organic chemistry procedures and a linear peptide chain were prepared.

The peptide-resin precursors for their respective short chain peptides may be cleaved and deprotected using suitable variations of any of the standard cleavage procedures described in the literature (King D. S., et al., Int. J. Peptide Protein Res., 1990, 36, 255-266). A preferred method for use in this invention is the use of TFA cleavage mixture, in the presence of water and TIPS as scavengers. Typically, the peptidyl-resin was incubated in TFA/Water/TIPS (95:2.5:2.5) for 1.5-4 hrs at room temperature. The cleaved resin is then filtered off and the TFA solution is concentrated or dried under reduced pressure. The resulting crude peptide is either precipitated or washed with $Et_2O$ or is re-dissolved directly into DMF or 50% aqueous acetic acid for purification by preparative HPLC.

Short chain peptides with the desired purity can be obtained by purification using preparative HPLC. The solution of crude peptide is injected into a semi-Prep column (Luna 10μ; $C_{18}$; 100 A°), dimension 250×50 mm and eluted with a linear gradient of ACN in water, both buffered with 0.1% TFA, using a flow rate of 40 ml/min with effluent monitoring by PDA detector at 220 nm. The structures of the purified short chain peptides can be confirmed by Electrospray Mass Spectroscopy (ES-MS) analysis.

All the peptide prepared were isolated as trifluoro-acetate salt, with TFA as a counter ion, after the Prep-HPLC purification. However, some peptides were subjected for desalting, by passing through a suitable ion exchange resin bed, preferably through anion-exchange resin Dowex SBR P(Cl) or an equivalent basic anion-exchange resin. In some cases, TFA counter ions were replaced with acetate ions, by passing through suitable ion-exchange resin, eluted with dilute acetic acid buffer. For the preparation of the hydrochloride salt of peptides, in the last stage of the manufacturing, selected peptides, with the acetate salt was treated with 4 M HCl. The resulting solution was filtered through a membrane filter (0.2 μm) and subsequently lyophilized to yield the white to off-white HCl salt. Following similar techniques and/or such suitable modifications, which are well within the scope of persons skilled in the art, other suitable pharmaceutically acceptable salts of the short chain peptides of the present invention were prepared.

General Method of Preparation of Short Chain Peptides, Using SPPS Approach:
Assembly of Short Chain Peptides on Resin:

Sufficient quantity (50-100 mg) of Fmoc-PAL-PEG-PS resin or Fmoc-Rink amide MBHA resin, loading: 0.5-0.6 mmol/g was swelled in DMF (1-10 ml/100 mg of resin) for 2-10 minutes. The Fmoc-group on resin was removed by incubation of resin with 10-30% piperidine in DMF (10-30 ml/100 mg of resin), for 10-30 minutes. Deprotected resin was filtered and washed excess of DMF, DCM and ether (50 ml×4). Washed resin was incubated in freshly distilled DMF (1 ml/100 mg of resin), under nitrogen atmosphere for 5 minutes. A 0.5 M solution of first Fmoc-protected amino acid (1-3 eq.), pre-activated with HOBt (1-3 eq.) and DIPCDI (1-2 eq.) in DMF was added to the resin, and the resin was then shaken for 1-3 hrs, under nitrogen atmosphere. Coupling completion was monitored using a qualitative ninhydrin test. After the coupling of first amino acid, the resin was washed with DMF, DCM and Diethyl ether (50 ml×4). For the coupling of next amino acid, firstly, the Fmoc-protection on first amino acid, coupled with resin was deprotected, using a 10-20% piperidine solution, followed by the coupling the Fmoc-protected second amino acid, using a suitable coupling agents, and as described above. The repeated cycles of deprotection, washing, coupling and washing were performed until the desired peptide chain was assembled on resin, as per general (Scheme 1) above. Finally, the Fmoc-protected peptidyl-resin prepared above was deprotected by 20% piperidine treatment as described above and the peptidyl-resins were washed with DMF, DCM and Diethyl ether. Resin containing desired peptide was dried under nitrogen pressure for 10-15 minutes and subjected for cleavage/deprotection.

Using above protocol and suitable variations thereof which are within the scope of a person skilled in the art, the short chain peptides designed in the present invention were prepared, using Fmoc-SPPS approach. Furthermore, resin bound short chain peptides were cleaved and deprotected, purified and characterized using following protocol.

Cleavage and Deprotection:

The desired short chain peptides were cleaved and deprotected from their respective peptidyl-resins by treatment with TFA cleavage mixture as follows. A solution of TFA/Water/Triisopropylsilane (95:2.5:2.5) (10 ml/100 mg of peptidyl-resin) was added to peptidyl-resins and the mixture was kept at room temperature with occasional starring. The resin was filtered, washed with a cleavage mixture and the combined filtrate was evaporated to dryness. Residue obtained was dissolved in 10 ml of water and the aqueous layer was extracted 3 times with ether and finally the aqueous layer was freeze-dried. Crude peptide obtained after freeze-drying was purified by preparative HPLC as follows:

Preparative HPLC Purification of the Crude Short Chain Peptides:

Preparative HPLC was carried out on a Shimadzu LC-8A liquid chromatography. A solution of crude peptide dissolved in DMF or water was injected into a semi-Prep column (Luna 10µ; $C_{18}$; 100 A°), dimension 250×50 mm and eluted with a linear gradient of ACN in water, both buffered with 0.1% TFA, using a flow rate of 15-50 ml/min, with effluent monitoring by PDA detector at 220 nm. A typical gradient of 20% to 70% of water-ACN mixture, buffered with 0.1% TFA was used, over a period of 50 minutes, with 1% gradient change per minute. The desired product eluted were collected in a single 10-20 ml fraction and pure short chain peptides were obtained as amorphous white powders by lyophilisation of respective HPLC fractions.

HPLC Analysis of the Purified Short-Chain Peptides

After purification by preparative HPLC as described above, each peptide was analyzed by analytical RP-HPLC on a Shimadzu LC-10AD analytical HPLC system. For analytical HPLC analysis of short chain peptides, Luna 5µ; $C_{18}$; 100 A°, dimension 250×4.6 mm column was used, with a linear gradient of 0.1% TFA and ACN buffer and the acquisition of chromatogram was carried out at 220 nm, using a PDA detector.

Characterization by Mass Spectrometry

Each peptide was characterized by electrospray ionisation mass spectrometry (ESI-MS), either in flow injection or LC/MS mode. Triple quadrupole mass spectrometers (API-3000 (MDS-SCIES, Canada) was used in all analyses in positive and negative ion electrospray mode. Full scan data was acquired over the mass range of quadrupole, operated at unit resolution. In all cases, the experimentally measured molecular weight was within 0.5 Daltons of the calculated monoisotopic molecular weight. Quantification of the mass chromatogram was done using Analyst 1.4.1 software.

Following table 1(i) is the list of short chain peptides synthesized using the SPPS approach as described above. Mentioned Seq. ID. No 1 in the list was taken as a reference from WO 2011027257.

TABLE 1 (i)

List of short chain peptides prepared

| Seq. ID. No. | Sequence of short chain peptides |
|---|---|
| 1 | SIPWNLERITPC |
| 2 | S-Nle-PWNLERITPC |
| 3 | S-Aib-PWNLERITPC |
| 4 | SIPWNLER-Nle-TPC |
| 5 | SIPWNLER-Aib-TPC |
| 6 | SIPWNLE-Har-ITPC |
| 7 | SIPWN-Nle-ERITPC |
| 8 | SI-Hyp-WNLERITPC |
| 9 | SIPWNLERIT-Hyp-C |
| 10 | SIPWN-Aib-ERITPC |
| 11 | Ac-SIPWNLERITPC |
| 12 | SIPWNLE-Cit-ITPC |
| 13 | SIPWNLERI-Aib-PC |
| 14 | Aib-IPWNLERITPC |
| 15 | S-(N-Me-Ile)-IPWNLERITPC |
| 16 | SIPWN-(N-Me-Leu)-ERITPC |
| 17 | SIPWNLER-(N-Me-Ile)-TPC |
| 18 | SIP-APPA-NLERITPC |
| 19 | SIP-Bip(OMe)-NLERITPC |
| 20 | SI-Hyp-WNLER-Aib-TPC |
| 21 | SI-Hyp-WN-Aib-ERITPC |
| 22 | SIPWNLE-Cit-Aib-TPC |
| 23 | SIPWN-Aib-E-Cit-ITPC |
| 24 | SI-Hyp-WNLE-Cit-ITPC |
| 25 | SI-Hyp-WN-Aib-E-Cit-ITPC |
| 26 | SI-Hyp-WNLE-Cit-Aib-TPC |
| 27 | SIPWNLE-Cit-IT-Hyp-C |
| 28 | SIPWN-Aib-ERIT-Hyp-C |
| 29 | SI-Hyp-WN-Aib-ERIT-Hyp-C |
| 30 | SIPWN-Aib-E-Cit-IT-Hyp-C |
| 31 | SI-Hyp-WNLE-Cit-IT-Hyp-C |
| 32 | SI-(αMe-Pro)-WNLE-Cit-ITPC |
| 33 | SI-AC$_3$C-WNLE-Cit-ITPC |
| 34 | SI-AC$_5$C-WNLE-Cit-ITPC |
| 35 | SI-AC$_6$C-WNLE-Cit-ITPC |

TABLE 1 (i)-continued

List of short chain peptides prepared

| Seq. ID. No. | Sequence of short chain peptides |
|---|---|
| 36 | SI-Hyp-WN-βAla-E-Cit-ITPC |
| 37 | SI-Hyp-WNL-(αMe-Glu)-Cit-ITPC |
| 38 | SI-Hyp-WNL-(Homo-Glu)-Cit-ITPC |
| 39 | SI-Hyp-WNL-(αMe-Asp)-Cit-ITPC |
| 40 | SI-Hyp-WN-HoLeu-E-Cit-ITPC |
| 41 | SI-Hyp-WN-(αMe-Asp)-E-Cit-ITPC |
| 42 | SI-Thz-WNLE-Cit-ITPC |
| 43 | SI-(2-Thz)-WNLE-Cit-ITPC |
| 44 | SI-(3-Hyp)-WNLE-Cit-ITPC |
| 45 | SI-Amp-WNLE-Cit-ITPC |
| 46 | SI-(3-Amp)-WNLE-Cit-ITPC |
| 47 | SI-(3-F-Pro)-WNLE-Cit-ITPC |
| 48 | SI-(4-F-Pro)-WNLE-Cit-ITPC |
| 49 | Ser(OMe)-I-Hyp-WNLE-Cit-ITPC |
| 50 | HoSer-I-Hyp-WNLE-Cit-ITPC |
| 51 | Thr(OMe)-I-Hyp-WNLE-Cit-ITPC |
| 52 | HoSer(OMe)-I-Hyp-WNLE-Cit-ITPC |
| 53 | SI-Hyp-(2F-Phe)-NLE-Cit-ITPC |
| 54 | SI-Hyp-(αMe-Phe)-NLE-Cit-ITPC |
| 55 | SI-Hyp-(αMe-2F-Phe)-NLE-Cit-ITPC |
| 56 | SI-Hyp-(αMe-2,6-diF-Phe)-NLE-Cit-ITPC |
| 57 | SI-Hyp-(αMe-APPA)-NLE-Cit-ITPC |
| 58 | SI-Hyp-WNL-Abu(CN)-Cit-ITPC |

In another preferred embodiment the peptides of the present invention can be chemically synthesized by methods which are well known in the art. It is also possible to produce the peptides of the present invention using recombinant methods. The peptides can be produced in microorganisms such as bacteria such as *E. coli, B. subtilis,* or any other bacterium that is capable of expressing such peptides, yeast such as *Saccharomyces cerevisiae, Schizosaccharomyces pombe, Candida, Pichia pastoris* or any other yeast capable of expressing peptides or fungi, in eukaryotic cells such as mammalian or insect cells, or in a recombinant virus vector such as adenovirus, poxvirus, herpes virus, Simliki forest virus, baculovirus, bacteriophage, sindbis virus or Sendai virus. Also methods for isolating and purifying recombinantly produced peptides are well known in the art and include e.g. gel filtration, affinity chromatography, ion exchange chromatography etc.

Procedure for DT Conjugation:

Diptheria toxin is a single polypeptide chain consisting of 535 amino acids, containing two subunits linked by disulfide bridges. One of the subunits binds to the cell surface, allowing the more stable subunit to penetrate the host cell. For conjugation, Diptheria toxoid and peptide need to be in equimolar concentration. Concentration of DT and peptide is 2-50 mg/mL. In the first step the Diptheria toxoid is brought into solution by dissolving it in Phosphate buffered saline. Next, EDAC (1-ethyl 3,3 dimethylaminopropyl carbodiimide) was added that provides the first step in crosslinking carboxylic acids. EDAC activates carboxyl groups for direct reaction with primary amines via the amide bond formation, thus primes the Diptheria toxoid for conjugation with peptide. Moreover, EDAC-mediated cross-linking is more effective in acidic pH. Hence, the reaction is allowed to take place by incubating DT with EDAC for one minute in the presence of MES buffer (40-morpholinoethane sulfonic acid) at pH 6.0. Moreover, this EDAC coupling method in the presence of MES improves the efficiency of the conjugation by forming intermediates. Next, ADH (Adipic Acid Dihydrazide) was added, which is a homobifunctional cross-linking reagent that results in relatively stable hydrazone linkages to the DT and peptide. Linking is carried out in a site-specific fashion, by oxidation first and then cross-linking, performed at pH 5.0 (due to the low pKa of the hydrazide). This avoids competition by primary amines. EDAC is again added, and the mixture is incubated for 3 hours at 2-8° C. to allow the conjugation to commence. The above prepared DT conjugated peptide is dialyzed through a 10 kD column and sterile filtered (0.2µ filter) for the removal of impurities, and the pure peptide-DT conjugate is stored at 2-8° C. for at least a week.

In another embodiment, conjugation is done with CRM197 which is genetically detoxified form of diphtheria toxin by following the general procedure given in WO 2011027257 and prior art.

In a further preferred embodiment the vaccine of the present invention may be administered subcutaneously, intramuscularly, intradermally, intravenously (see e.g. "Handbook of Pharmaceutical Manufacturing Formulations", Sarfaraz Niazi, CRC Press Inc, 2004). The formulation may consist of respective carriers, adjuvants, and/or excipients depending on the route of administration.

Vaccine Formulations:

For the design of more immunopotent and protective vaccines, the final vaccine formulation may contain adjuvants with immunopotentiating properties that can direct the immune responses to humoral or cell-mediated immunity, depending on the type of adjuvant. Traditional adjuvants such as aluminum salts, emulsions, liposomes and virosomes present vaccine antigens to the immune system in an efficient manner and control the release and storage of antigens to increase the specific immune response. The second class of adjuvants is immunostimulants, which affect the immune system and increase the immune responses to antigens. For example, they influence cytokine production through the activation of MHC molecules, co-stimulatory signals, or through related intracellular signaling pathways.

It has been found that many of the currently approved vaccine adjuvants are not always sufficiently potent to induce an efficient protective immune response against different target pathogens, particularly in immunologically hyporesponsive populations such as the elderly and immunocompromised populations, where there is a decreased T-cell dependent antibody response because of compromised T-cell function. The use of adjuvants with immunopotentiating properties yield a more effective response in a large number of vaccines such as hepatitis C virus (HCV), HIV, HBV, HPV, influenza and cancer. A more rational approach to vaccine design therefore is the use of immunostimulant adjuvants that can modulate and enhance cytotoxic T lymphocyte (CTL) responses, and/or affect dendritic cells (DCs) through TLR exploitation. T cells are the most effective arm of the immune response and given the recognized importance of T cells in regulating immune responses to vaccination, use of these novel adjuvants in vaccination strategies seems fitting.

Other Adjuvants that can be Used for the Formulation:

In Order to elicit stronger immune response from the DT-conjugated peptide, additional adjuvants added to the formulation are as below.

1) Alum (aluminum hydroxide gel, 2% wet gel suspension)
   Alum is an effective adjuvant as the antigen is adjuvanted with insoluble aluminum salts, that remain in the body for a long time. The antigen is slowly released from the insoluble salt particles, allowing prolonged and effective stimulation of the immune system ('depot effect') [1]. In addition to or in contrast to the depot effect, insoluble aluminium salts activate innate immune cells in a manner that ultimately results in a T helper 2 (Th2)-type immune response Alum induces a Th2 response by improving antigenic uptake of antigen by antigen-presenting cells (APCs)[2].

2) Alum with MF-59
   AddaVax (also known as MF59) is a squalene-based oil-in-water nano-emulsion. Squalene is an oil more readily metabolized than the paraffin oil used in Freund's adjuvants [3]. Squalene oil-in-water emulsions elicit both cellular (Th1) and humoral (Th2) immune responses [4, 5]. This adjuvant class acts via recruitment and activation of Antigen presenting cells along with stimulation of cytokine and chemokine production by macrophages and granulocytes [3].

3) Alum with other adjuvants like TLR3 agonist such as Poly(I:C), TLR 4 agonist such as Monophosphoryl Lipid A or GLA-SE, TLR5 agonist such as Flagellin, TLR7 agonist such as Gardiquimod and Imiquimod TLR7/8 agonist such as R848, NOD2 agonist such as N-glycolyl-MDP.CpG-containing nucleic acid (where the cytosine is unmethylated), QS21 (saponin adjuvant), interleukins, beta-sitosterol and the like.
   An adjuvant used in all the experiments is combination of alum and stable formulation of Monophosphoryl Lipid A.

Affinity Determination of New Peptides:

Affinity parameters of new peptides for recombinant human PCSK9 were analyzed by surface plasmon resonance (SPR), using a Biacore instrument (Biacore T200, GE Healthcare). SPR experiments were performed at 25° C. with a BIACORE T200 apparatus (GE Healthcare, Uppsala, Sweden).

Surface Preparation: (Procedure for Protein Immobilization)

Purified recombinant human PCSK9 (His-tagged, BPS Biosciences) diluted to 100-150 µg/mL in 10 mM acetate buffer, pH 5.0, was immobilized on one of the four flow cells of a Series S Sensor Chip CMS to a level of approximately 6000 to 8000 RU (resonance units) by the use of amine-coupling chemistry. The surface was blocked with 1M ethanolamine, pH 8.5. Whereas one flow cell was immobilized as blank for reference subtraction (no PCSK9). 10 mM Hepes (pH 7.4) with 150 mM NaCl was used as running buffer. The rest two flow cells were saved for future use.

Binding and Kinetics/Affinity Experiments:

100× Stock solutions of NCE (new peptides) were made in 100% DMSO and were diluted to range of concentrations in 10 mM Hepes, pH7.4+150 mM NaCl so that the final conc of DMSO is kept at 1%. Binding/Kinetics studies were conducted by passing various concentrations of NCEs over blank as well as ligand (protein) immobilized surface. Each cycle consisted of a 60 s or 120 s analyte (diluted small molecule drug) injection at flow rate with between 5 to 30 µL/min (the association phase), followed by a dissociation phase with between 60 to 180 s. If required, regeneration was done using a 30 s (15 µL) injection of 10 mM glycine/HCl (pH 1.5) and 20 s or 30 s (10 or 15 µL) injection of 10 mM NaOH. The data were analyzed using the Biacore T200 Evaluation software. All the curves were reference-subtracted. Baselines were adjusted to zero for all curves and data were presented as binding RU (Average of 5 s window) 5 s before end of sample injection.

For $K_D$ (equilibrium dissociation constant) determinations analyte curves were subtracted from buffer blank and modeled assuming a simple 1:1 interaction to generate the kinetic data.

Immunogenicity Study in BALB/c Mice

Female BALB/c mice of 12-15 weeks of age issued from animal house and kept for 2-3 acclimatization. Mice had access to food and water ad libitum and were kept under a 12 hrs light/dark cycle. On Day-0 (pre-treatment) animals bled and serum was harvested for total cholesterol measurement. Animals were randomized and grouped to various treatments based on their total cholesterol and body weights. On next day of Day-0 (pre-treatment) blood collection animals were immunised with 0.3 ml of vaccine formulations as mentioned Table No. 1 by subcutaneous or intramuscular route. Next booster injection was given on 2 weeks and 4 weeks after first injection and animals were bled for immunogenicity measurement on two weeks thereafter till week 7 and then every four week till 32 week, detailed schedule of blood collection was Day-0 (pre-treatment) from there $5^{th}$, $7^{th}$, $20^{th}$, $24^{th}$, $28^{th}$, $32^{nd}$, $45^{th}$ and $57^{th}$ week after first vaccine administration. Serum was separated and serum total cholesterol was measured and immunogenicity or antibody confirmation was done using ELISA for PCSK9 antibody titer, binding of serum antibodies with human PCSK9 using Surface plasmon resonance (SPR) assay and LDLR-PCSK9 interaction inhibition assay.

TABLE NO. 1

| Groups | Treatment | Number of Animals |
|---|---|---|
| 1 | Phosphate Buffer Saline (PBS) | 8 |
| 2 | Placebo (PBS + adjuvant) | 8 |
| 3 | DT conjugated Seq. ID. No. 1 in adjuvant | 8 |
| 6 | DT conjugated Seq. ID. No. 7 in adjuvant | 8 |
| 7 | DT conjugated Seq. ID. No. 8 in adjuvant | 8 |
| 8 | DT conjugated Seq. ID. No. 12 in adjuvant | 8 |

Immunogenicity Study in hApoB100/hCETP Double-Transgenic Mice (dTg)

Male or female hApoB100/hCETP dTg mice of more than 8 weeks of age issued from animal house and kept for 2-3 acclimatization. Mice had access to food and water ad libitum and were kept under a 12 hrs light/dark cycle. On Day-0 (pre-treatment) animals bled and serum was harvested for LDL-cholesterol (LDL-C), total cholesterol, HDL-C and triglycerides measurement. Animals were randomized and grouped to various treatments based on their LDL-C and body weights. On next day of blood collection animals were immunised with 0.3 ml of vaccine formulations by subcutaneous or intramuscular route. Next booster injection was given on 2 weeks and 4 weeks after first injection and animals were bled for immunogenicity measurement on two weeks after third injection. Serum was separated and serum LDL-C, total cholesterol, HDL-C and triglycerides levels were measured and immunogenicity or antibody confirmation was done using ELISA for PCSK9 antibody titer, binding of serum antibodies with human PCSK9 using Surface plasmon resonance (SPR) assay and LDLR-PCSK9 interaction inhibition assay.

Serum LDL-C, HDL-C, total cholesterol and triglycerides levels were determined using commercial kits (Roche Diagnostics, Germany) on a Cobas c311 autoanalyzer (Roche, Germany).

Evaluation of Humoral Response by Anti-PCSK-9 ELISA

At specific intervals of time (15 days post immunization with each booster), serum samples were collected from all groups of mice. 96-well ELISA plates (#442402) were pre-coated with PCSK-9 protein 50 ng/well and plate incubated overnight at 2-8° C. Next day, wells were washed to remove unbound protein and blocked in 2% skimmed milk-PB ST for 2 hours, and washed with PBST. Sera samples were diluted 1:20 with 0.2% skimmed milk made in PBST. Appropriate volume of samples and standards was added to each well, and incubated for 1 hour at 37° C. Anti-mouse IgG secondary HRP-labeled antibody was added to each well and incubated at 37° C. for 1 hour, then washed. OPD-substrate was added to each well and incubated for 20 minutes at room temperature in the dark. Plates were read at 492 nm on a Spectramax microplate reader. Amongst all the DT-conjugated PCSK-9 peptides tested, the one that gave the highest response was treated as the standard, and its placebo was used to calculate the corrected OD. The sera from the mice injected with PBS were used as negative control. By using the negative control value, cut-off value was calculated and the corrected OD's above the cut off value were treated as standards. All test samples gave absolute antibody titres against PCSK-9, extrapolated from the standard curve and values were expressed in log 10.

LDLR-PCSK9 Interaction Inhibition Assay:

Inhibition of LDLR-PCSK9 interaction by antibody (Ab) in serum from vaccine treated animal were assayed using BPS Bioscience in-vitro PCSK9[Biotinylated]-LDLR Binding Assay Kit (BPS Bioscience, San Diego, Calif., USA) with minor modifications. First, LDLR ectodomain is coated on a 96-well plate and plate was incubated overnight. Next, PCSK9-biotin was diluted in 1×PCSK9 assay buffer to obtain 2.5 ng/µl (50 ng/20 µl) concentration and this master mix, test inhibitor (serum samples from animal studies), inhibitor buffer was added to LDL-R coated plate and incubated at room temperature for 2 hours. Finally, the plate is treated with streptavidin-HRP followed by addition of an HRP substrate to produce chemiluminescence, which was then measured using a chemiluminescence reader according to the manufacturer's instructions. Relative inhibition was denoted as the difference in percentage inhibition between the intensity of the PCSK9-LDLR binding in the serum samples from vaccine treated animals and that in placebo treated which was considered as 100%.

Results:

I) Table No. 2 Affinity of new peptides for recombinant human PCSK9 analyzed by surface plasmon resonance (SPR), using a Biacore (Biacore T200, GE Healthcare).

TABLE NO. 2

Affinity study of new peptides for recombinant human PCSK9.

| Seq. ID. No. | Binding - Response Unit(RU) | Binding- Response Unit(RU) |
|---|---|---|
| 1 | 7.4 (50 µM) | — |
| 4 | 13.05 (50 µM) | 30.00 (100 µM) |
| 5 | 2.30 (50 µM) | 7.10 (100 µM) |
| 6 | 6.55 (50 µM) | 17.50 (100 µM) |
| 7 | 6.65 (50 µM) | 16.00 (100 µM) |
| 8 | 5.70 (50 µM) | 13.25 (100 µM) |
| 10 | 3.00 (50 µM) | 7.50 (100 µM) |
| 12 | 3.10 (50 µM) | 6.70 (100 µM) |
| 13 | 9.75 (50 µM) | 37.35 (100 µM) |
| 14 | 7.10 (50 µM) | 15.00 (100 µM) |
| 15 | 11.45 (50 µM) | 29.85 (100 µM) |
| 18 | 10.20 (50 µM) | 17.85 (100 µM) |
| 19 | 35.15 (50 µM) | 85.90 (100 µM) |

II) The mean antibody titers against PCSK9 in serum samples of treated animals measured by ELISA assay given in below Table no. 3

TABLE NO. 3

Mean Antibody titers against PCSK9 in ELISA Assay

| Antibody Titers against PCSK9 in ELISA | Weeks after Vaccine Administration | | | | | | | |
|---|---|---|---|---|---|---|---|---|
| Tests groups | WK-5 | WK-7 | WK-20 | WK-24 | WK-28 | WK-32 | WK-45 | WK-57 |
| DT conjugation Seq. ID. No. 1 in adjuvant | 20664 | 58298 | 285 | 17389 | 4879 | 178599 | 179876 | 184408 |
| DT conjugation Seq. ID. No. 7 in adjuvant | 22773 | 424261 | 79448 | 38510 | 11553 | 320988 | 351529 | 405753 |
| DT conjugation Seq. ID. No. 8 in adjuvant | 39040 | 199806 | 100413 | 80141 | 14264 | 297967 | 356639 | 780136 |
| DT conjugation Seq. ID. No. 12 in adjuvant | 48964 | 698079 | 155994 | 116790 | 64880 | 510187 | 1140238 | 744605 |

All the peptide formulations showed very high levels of antibody titers against human PCSK9 and titers were higher for peptides of Seq. ID. No. 7, 8, 12 as compared to Seq.ID.No.1. Very high antibody response was maintained till 57th week after vaccine administration, demonstrating the possibility of immunogenic response for more than a year for a few of the peptide formulations.

III) Inhibition of LDLR-PCSK9 interaction by antibody (Ab) in serum from vaccine treated animal were assayed using in-vitro PCSK9 [Biotinylated]-LDLR Binding Assay Kit as measure of functional assay. The percent inhibition LDLR-PCSK9 interaction by antibody (Ab) was measured once at week-5, given in Table no. 4.

TABLE NO. 4

LDLR-PCSK9 interaction inhibition by ELISA assay

| LDLR- PCSK-9% interaction Inhibition Vs. Placebo Tests groups | Weeks after Vaccine Administration WK-5 |
|---|---|
| DT conjugation Seq. ID. No. 1 in adjuvant | 46 |
| DT conjugation Seq. ID. No. 7 in adjuvant | 66 |
| DT conjugation Seq. ID. No. 8 in adjuvant | 66 |
| DT conjugation Seq. ID. No. 12 in adjuvant | 67 |

Almost all the peptide formulations showed 40-70% inhibition LDLR-PCSK9 interaction at week 5. The interaction inhibition shown by Seq. ID. No. 7, 8, 12 were significantly higher than that of Seq. ID No.1

IV) The antibody detection in serum samples of treated animals was also confirmed by affinity determination against human PCSK9 using SPR assay given in below Table no. 5

TABLE NO. 5

Serum Antibody Detection by Affinity Determination against human PCSK9 using SPR assay.

| Surface plasmon response(SPR) Response Unit (RU) Tests groups | Weeks after Vaccine Administration | | | | | |
|---|---|---|---|---|---|---|
| | WK-5 Avg. | WK-7 Avg. | WK-20 Avg. | WK-24 Avg. | WK-45 Avg. | WK-57 Avg. |
| DT conjugation Seq. ID. No. 1 in adjuvant | 19 | 8 | 37 | 35 | 29 | 23 |
| DT conjugation Seq. ID. No. 7 in adjuvant | 40 | 29 | 61 | 58 | 41 | 35 |
| DT conjugation Seq. ID. No. 8 in adjuvant | 49 | 30 | 59 | 57 | 47 | 42 |
| DT conjugation Seq. ID. No. 12 in adjuvant | 48 | 33 | 61 | 61 | 55 | 49 |

The serum of samples from animals treated with peptide formulations showed increase in response unit as compared to placebo. On week 5 and week-57, sequence ID. No. 12 showed significantly higher antibody response and sequence ID. No. 8 showed significantly higher antibody response on week-5 as compared to Seq.ID.No. No. 1. There was very high antibody response maintained till 57$^{th}$ week after vaccine administration; it clearly demonstrates the possibility of immunogenic response for more than a year for peptide formulations The peptides of the present invention are administered to a mammal or an individual in an amount of 0.1 ng to 10 mg, preferably of 0.5 to 500 µg, per immunization. In a preferred embodiment these amounts refer to all peptides (if more than one peptide is used in the vaccine) present in the vaccine.

The amount of peptides that may be combined with the carrier materials to produce a single dosage form will vary depending upon the host treated and the particular mode of administration.

The dose of the vaccine may vary according to factors such as the disease state, age, sex and weight of the mammal or individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances. For instance, the peptides and vaccine of the present invention may be administered to an individual at intervals of several days, one or two weeks or even months or years depending always on the level of antibodies directed to PCSK9.

The peptides of the present invention can act as a vaccine when conjugated with suitable immunogenic carrier. These vaccines are able to form antibodies which bind to PCSK9 upon administration. These vaccines can be suitable for the prevention/treatment of disorders like hyperlipidaemia, hypercholesterolemia or atherosclerosis.

REFERENCES

1) Glenny A T, Pope C G, Waddington H, Wallace U. Immunological Notes: XVII-XXIV. J Pathol Bacteriol. 1926; 29:31-40.
2) Grun J L, Maurer P H. Different T helper cell subsets elicited in mice utilizing two different adjuvant vehicles: the role of endogenous interleukin 1 in proliferative responses. Cell Immunol. 1989; 121:134-145.
3) Ott G. et al., 2000. The adjuvant MF59: a 10-year perspective. Methods in Molecular Medicine, Vol 42, 211-228.
4) Calabro, S. et al., 2013. The adjuvant effect of MF59 is due to the oil-in-water emulsion formulation, none of the individual components induce a comparable adjuvant effect. Vaccine 31:3363-9.
5) Ott G. et al., 1995. MF59. Design and evaluation of a safe and potent adjuvant for human vaccines. Pharm Biotechnol 6: 277-96.

The invention claimed is:

1. A peptide comprising an amino acid sequence selected from the group consisting of:

SIPWNLER-Nle-TPC; [SEQ ID NO: 4]

SIPWNLER-Aib-TPC; [SEQ ID NO: 5]

SIPWNLE-Har-ITPC; [SEQ ID NO: 6]

SIPWN-Nle-ERITPC; [SEQ ID NO: 7]

SI-Hyp-WNLERITPC; [SEQ ID NO: 8]

SIPWN-Aib-ERITPC; [SEQ ID NO: 10]

SIPWNLE-Cit-ITPC; [SEQ ID NO: 12]

SIPWNLERI-Aib-PC; [SEQ ID NO: 13]

Aib-IPWNLERITPC; [SEQ ID NO: 14]

S-(N-Me-Ile)-IPWNLERITPC; [SEQ ID NO: 15]

SIP-APPA-NLERITPC; and [SEQ ID NO: 18]

SIP-Bip(OMe)-NLERITPC. [SEQ ID NO: 19]

2. The peptide of claim 1, wherein the amino acid sequence is conjugated with an immunogenic carrier selected from the group consisting of diphtheria toxin (DT), *Corynebacterium diphtheriae* (CRM) 197, keyhole limpet haemocyanin (KLH), tetanus toxoid (TT) and protein D.

3. The peptide as claimed in claim 1, wherein the amino acid sequence is conjugated with an immunogenic carrier, in combination with one or more pharmaceutically acceptable adjuvants and other pharmaceutical excipients.

4. The peptide as claimed in claim 1, wherein the amino acid sequence is conjugated with an immunogenic carrier and with one or more pharmaceutically acceptable adjuvants, wherein the pharmaceutically acceptable adjuvants are selected from the group of consisting of alum, Toll-like 3 receptors (TLR3) agonist, Poly(I:C), Toll-like 4 receptors (TLR4) agonist, Monophosphoryl Lipid A, Glucopyranosyl Lipid Adjuvant (GLA), Toll-like 5 receptors (TLR5) agonist, Flagellin, Toll-like 7 receptors (TLR7) agonist, Gardiquimod, imiquimod, TLR7/8 agonist, R848, Nucleotide-binding oligomerization domain-containing protein2 (NOD2) agonist, N-glycolyl-muramyl dipeptide (MDP), CpG-containing nucleic acid wherein the cytosine is unmethylated, QS21 (saponin adjuvant), interleukins, and beta-sitosterol.

5. The peptide as claimed in claim 1 suitable for the treatment of health disorders selected from hyperlipidaemia, hypercholesterolemia, atherosclerosis and other cardiovascular diseases.

* * * * *